US011312758B2

(12) United States Patent
Kini et al.

(10) Patent No.: US 11,312,758 B2
(45) Date of Patent: Apr. 26, 2022

(54) PEPTIDES WITH VASODILATORY AND/OR DIURETIC FUNCTIONS

(71) Applicant: National University of Singapore, Singapore (SG)

(72) Inventors: Manjunatha Ramachandra Kini, Singapore (SG); Sindhuja Sridharan, Chennai (IN)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 16/325,928

(22) PCT Filed: Aug. 18, 2017

(86) PCT No.: PCT/SG2017/050411
§ 371 (c)(1),
(2) Date: Feb. 15, 2019

(87) PCT Pub. No.: WO2018/034622
PCT Pub. Date: Feb. 22, 2018

(65) Prior Publication Data
US 2019/0211071 A1 Jul. 11, 2019

(30) Foreign Application Priority Data
Aug. 18, 2016 (SG) .......................... 10201606879W

(51) Int. Cl.
C07K 14/58 (2006.01)
C07K 4/12 (2006.01)
A61P 9/00 (2006.01)
A61P 9/12 (2006.01)
A61K 38/00 (2006.01)

(52) U.S. Cl.
CPC ................ *C07K 14/58* (2013.01); *A61P 9/00* (2018.01); *A61P 9/12* (2018.01); *C07K 4/12* (2013.01); *A61K 38/00* (2013.01)

(58) Field of Classification Search
None
See application file for complete search history.

(56) References Cited

U.S. PATENT DOCUMENTS

| | | |
|---|---|---|
| 2003/0069186 A1 | 4/2003 | Burnett, Jr. |
| 2006/0172933 A1 | 8/2006 | James et al. |
| 2008/0153747 A1 | 6/2008 | Alewood et al. |
| 2012/0164142 A1 | 6/2012 | Crine et al. |
| 2012/0238498 A1* | 9/2012 | Endo ................ A61P 37/08 514/12.4 |
| 2014/0005358 A1 | 1/2014 | Lee et al. |

FOREIGN PATENT DOCUMENTS

WO WO 2012/099258 7/2012
WO WO-2014/209229 A1 12/2014

OTHER PUBLICATIONS

Scholar Bank entry Sridharan thesis, retrieved from https://scholarbank.nus.edu.sg/handle/10635/53804?mode=full on Sep. 21, 2020, 2 pages (Year: 2020).*
CAS Registy No. 45307 03 1 entered Mar. 11, 2005, 6 pages (Year: 2005).*
Schoenfeld et al. ('Agonist selectivity for three species of natriuretic peptide receptor-A' Molecular Pharmacology v47 1995 pp. 172-180) (Year: 1995).*
International Search Report and Written Opinion for PCT/SG2017/050411, dated Oct. 27, 2017, 11 pages.
Potter, "Natriuretic Peptides: Their Structures, Receptors, Physiologic Functions and Therapeutic Applications," Handb. Exp. Pharmacol. (2009) 191(1):341-366.
Sridharan, S. Ph.D. Thesis: Structure-Function Relationships and Action Mechanism of Krait Natriuretic Peptide (Jun. 11, 2014), 170 pages.
Sridharan and Kini, "Tail wags the dog: activity of krait natriuretic peptide is determined by its C-terminal tail in a natriuretic peptide receptor-independent manner," Biochem. J. (2015) 469(2):255-266.
Sridharan and Kini, "Krait natriuretic peptide (KNP): a non-classical NP," BMC Pharmacology and Toxicology (2013) 14(Suppl. 1):P67.
Sridharan and Kini, "Decoding the molecular switches of natriuretic peptides which differentiate its vascular and renal functions," Biochemical Journal (2018) 475:399-413.
Sridharan et al., "Krait natriuretic peptide (KNP): a non-classical NP," BMC Pharmacology and Toxicology (2013) 14(Suppl 1): P67.
Sridharan et al. "Decoding the molecular switches of natriuretic peptides which differentiate its vascular and renal functions," Biochemical Journal (2018) 475(2):399-413.
Sridharan, S. Ph.D. Thesis: Structure-Function Relationships and Action Mechanism of Krait Natriuretic Peptide (Jul. 2, 2016), 170 pages.
Zhang et al., "Cardiovascular and renal effect of CNAAC: An innovatively designed natriuretic peptide," Eur J Pharmacol. (2015) 761:180-188.

* cited by examiner

*Primary Examiner* — Ronald T Niebauer
(74) *Attorney, Agent, or Firm* — Morrison & Foerster LLP

(57) ABSTRACT

The present invention relates to peptides with vasodilatory and/or diuretic functions. In particular, the invention relates to modifying key amino acid residues in natriuretic peptides to achieve different functions and properties. Accordingly the invention also includes modified natriuretic peptides. The invention also relates to the use of these peptides for regulating blood pressure-volume and/or treating a heart condition.

12 Claims, 8 Drawing Sheets
Specification includes a Sequence Listing.

| SEQ ID: 52 | ANP |
| SEQ ID: 53 | KNP |
| SEQ ID: 32 | K-Ring |
| SEQ ID: 54 | BNP |
| SEQ ID: 55 | CNP |
| SEQ ID: 56 | DNP |

| K-Ring variants | | Sequence | | Vascular response | Renal response |
|---|---|---|---|---|---|
| | | 3 | 14 | | |
| SEQ ID: 32 | K-Ring | GLLISCFDRRIDRISHTSDIGCRH | | + | − |
| SEQ ID: 33 | DRGK-Ring | GLLISCFDRRIDRISHTSGIGCRH | | + | − |
| SEQ ID: 34 | GRDK-Ring | GLLISCFGRRIDRISHTSDIGCRH | | + | − |
| SEQ ID: 35 | DGDK-Ring | GLLISCFDGRIDRISHTSDIGCRH | | + | − |
| SEQ ID: 36 | GRGK-Ring | GLLISCFGRRIDRISHTSGIGCRH | | + | + |
| SEQ ID: 37 | K-Ring^NSFRY | GLLISCFDRRIDRISHTSDIGCNSFRY | | + | + |

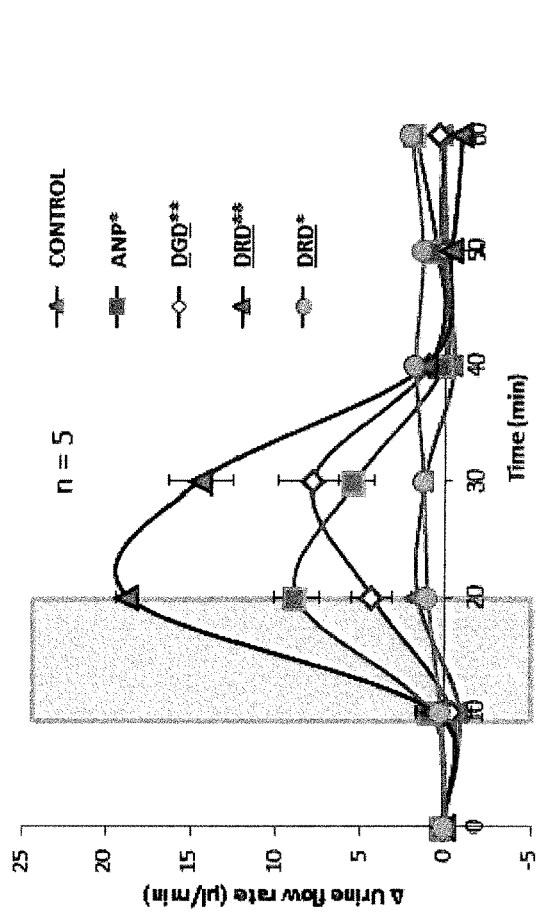
FIG. 3A
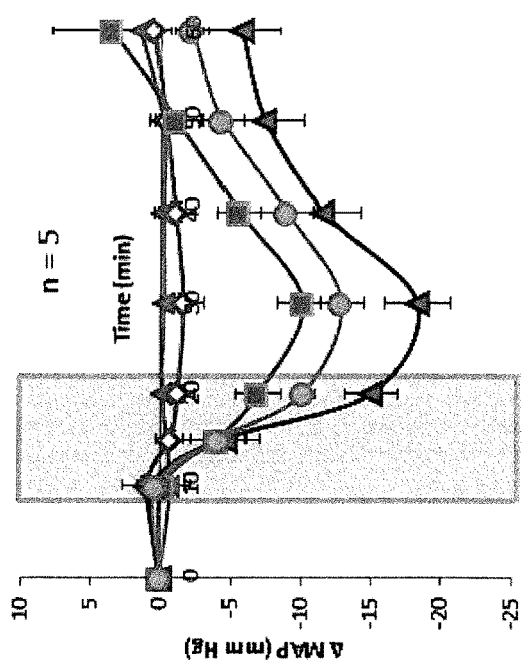
FIG. 3B
FIG. 3C

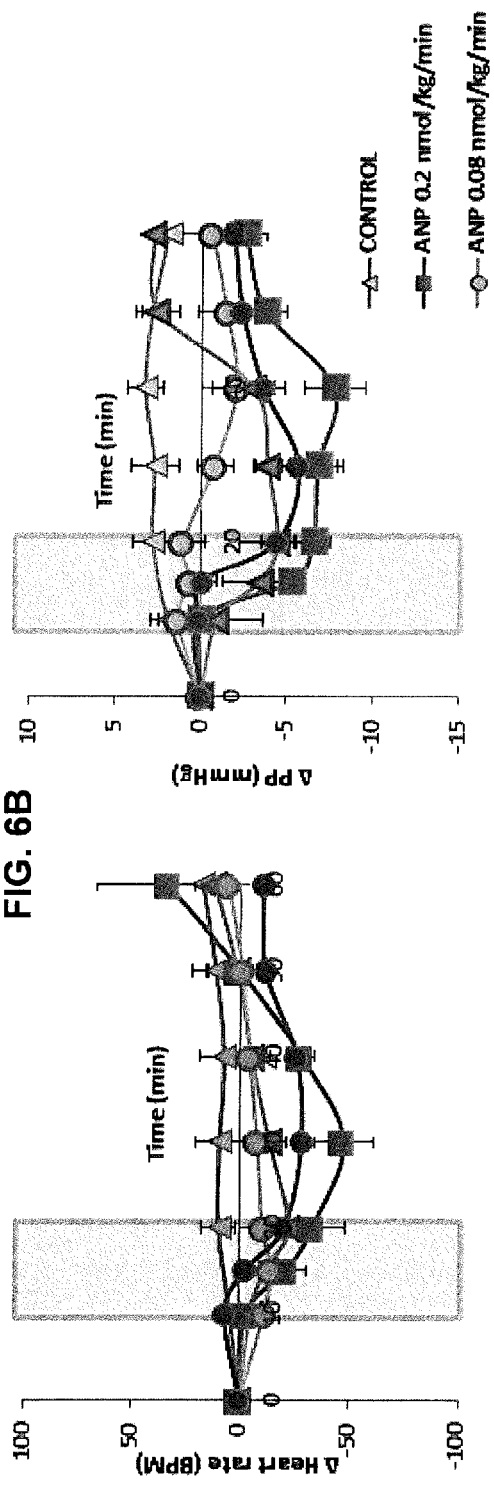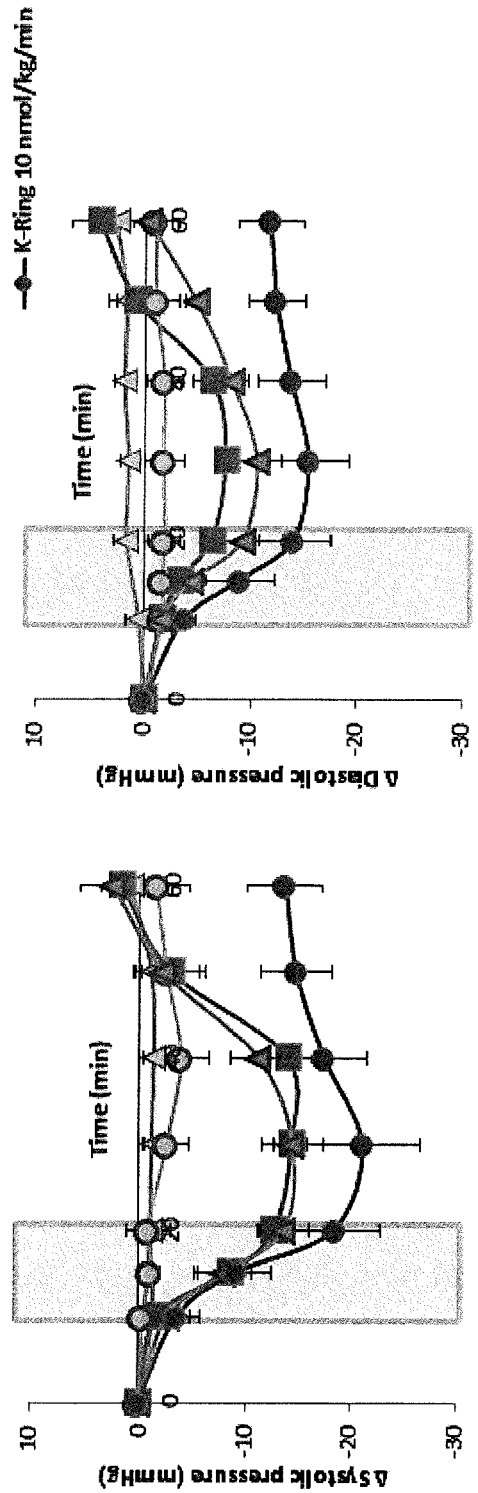

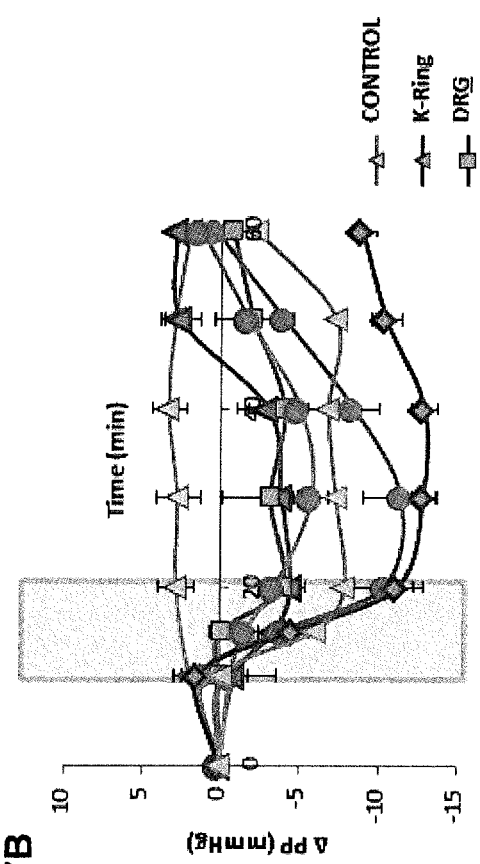
FIG. 7A
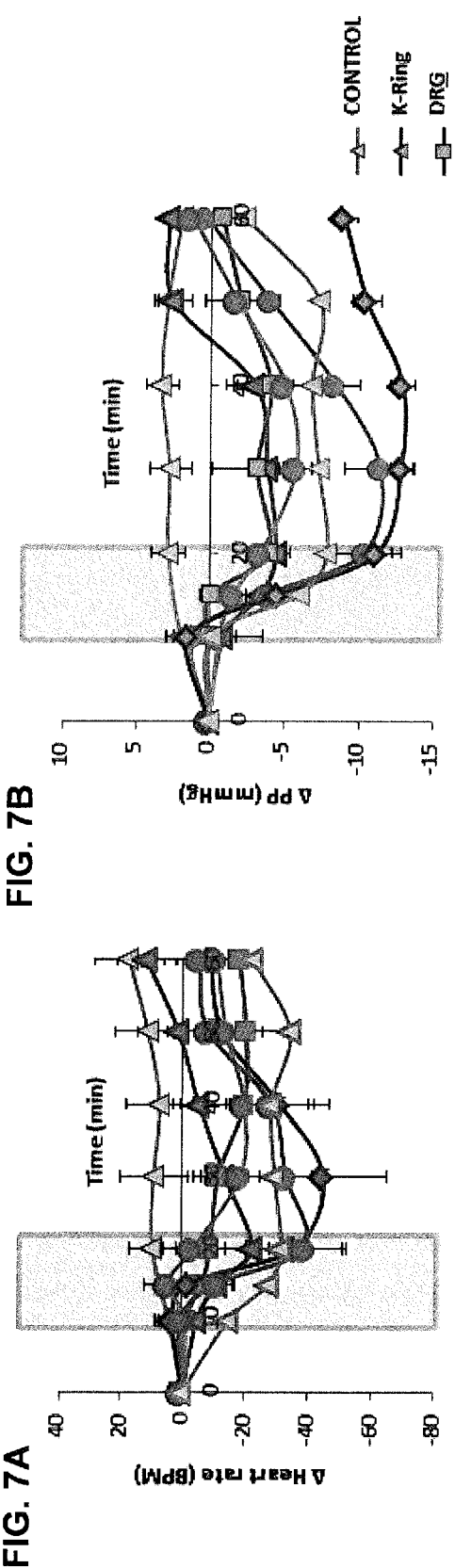
FIG. 7B
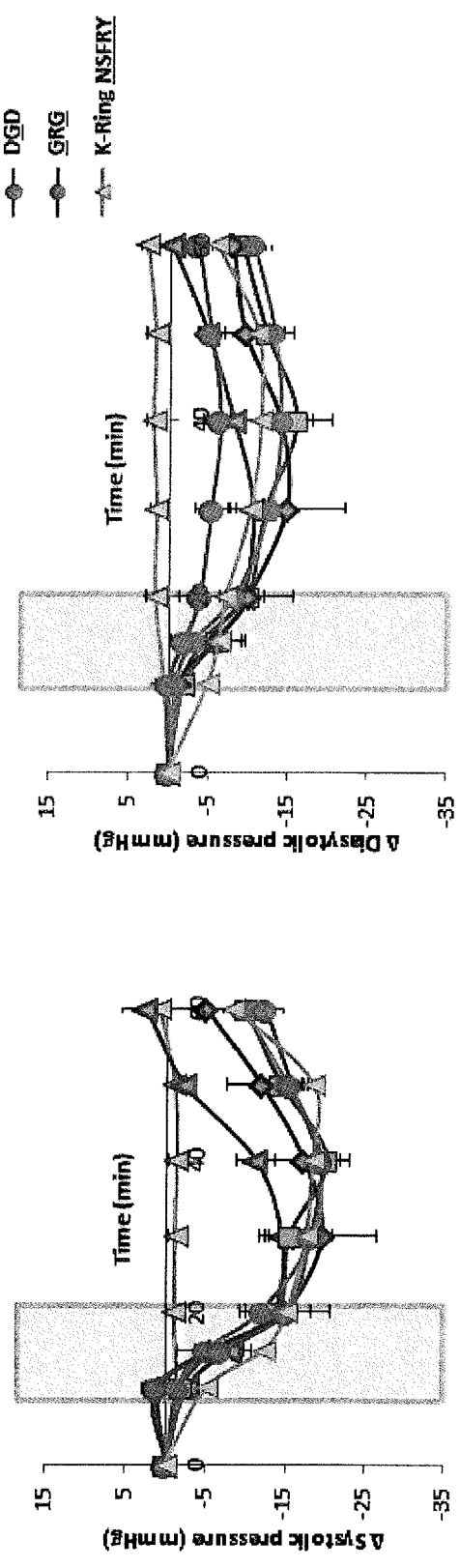
FIG. 7C
FIG. 7D

PEPTIDES WITH VASODILATORY AND/OR DIURETIC FUNCTIONS

CROSS REFERENCE TO RELATED APPLICATIONS

This application is a U.S. national phase of International Patent Application No. PCT/SG2017/050411, filed Aug. 18, 2017, entitled "PEPTIDES WITH VASODILATORY AND/OR DIURETIC FUNCTIONS," which claims the benefit of priority to Singapore Patent Application No. 10201606879W, filed Aug. 18, 2016, entitled "PEPTIDES WITH VASODILATORY AND/OR DIURETIC FUNCTIONS," the contents of which applications are hereby incorporated by reference in their entirety for all purposes.

INCORPORATION BY REFERENCE OF SEQUENCE LISTING

The present application is being filed along with a Sequence Listing in electronic format. The Sequence Listing is provided as a file entitled 255352004800SeqList.txt, created Jul. 5, 2020 which is 33,947 bytes in size. The information in the electronic format of the Sequence Listing is incorporated by reference in its entirety.

FIELD OF THE INVENTION

The present invention relates to peptides with vasodilatory and/or diuretic functions. The invention also relates to the use of these peptides for regulating blood pressure-volume.

BACKGROUND OF THE INVENTION

Heart failure (HF) is one of the leading causes of death in the world (1 in 4 deaths) [Roger, V. L.; et al., *Circulation* 123 (4): e18-e209 (2011)]. Although several factors such as coronary artery disease, myocardial infarction, prolonged hypertension, cardiomyopathy could initiate HF, the progression of the syndrome is linked to the activation of neurohumoral systems, specifically of that of (renin-angiotensin aldosterone system (RAAS) and sympathetic (SNS) which elevate blood volume and pressure [MacMahon, K. M.; Lip, G. Y., *Arch Intern Med* 162 (5): 509-16 (2002)]. The distinctive features of HF encompass functional and structural changes in the heart along with vasoconstriction, avid retention of water and sodium by kidney to various degrees [McMurray, J. J.; Pfeffer, M. A., *Lancet* 365 (9474): 1877-89 (2005)]. The patients with HF may be broadly classified into: (a) hypertensive HF with euvolemic or mildly hypervolemic, (b) normotensive HF with hypovolemic and (c) hypotensive HF with hypervolemic or hypovolemic states [Packer, M., *Am J Cardiol* 71 (9): 3C-11C (1993); Strobeck, J. E.; Silver, M. A., *Congest Heart Fail* 10 (2 Suppl 2): 1-6 (2004)].

Natriuretic peptides (NPs) are a class of vital hormones which confer cardiovascular protection through regulation of vascular tone and fluid volume in the body [Brenner, B. M.; et al., *Physiol Rev* 70 (3): 665-99 (1990)]. They have indispensable roles in influencing hemodynamics of an organism under physiological and pathological conditions. There are three isoforms of NPs—ANP, BNP and CNP, identified in mammals [Kangawa, K.; Matsuo, H., *Biochem Biophys Res Commun* 118 (1): 131-9 (1984); Sudoh, T.; et al., *Nature* 332 (6159): 78-81 (1988); Sudoh, T.; et al., *Biochem Biophys Res Commun* 168 (2): 863-70 (1990)]. These peptides have an evolutionarily conserved 17-residue ring held by a disulphide bond and a variable N- and C-terminal tails. ANP and BNP are secreted by the cardiac walls in response to increasing filling pressures in the chambers of the heart [de Bold, A. J., *Science* 230 (4727): 767-70 (1985)] while CNP is derived from vascular endothelium [Suga, S.; et al., *Endocrinology* 133 (6): 3038-41 (1993)]. These peptides bind to specific membrane bound natriuretic peptide receptors (NPR-A, NPR-B or NPR-C). ANP and BNP activate NPR-A [Waldman, S. A.; et al., *J Biol Chem* 259 (23): 14332-4 (1984)] and CNP functions through NPR-B to elevate intracellular cGMP levels [Suga, S.; et al., *Endocrinology* 130 (1): 229-39 (1992)]. The downstream activities of ANP/NPR-A signaling include vasodilation, increased excretion of water and electrolytes through kidneys, increased endothelial permeability and inhibition of renin-angiotensin aldosterone system (RAAS) and sympathetic nervous system (SNS) [Brenner, B. M.; et al., *Physiol Rev* 70 (3): 665-99 (1990); Maack, T.; et al., *Fed Proc* 45 (7): 2128-32 (1986); Sasaki, A.; et al., *Eur J Pharmacol* 109 (3): 405-7 (1985)]. These direct effects on hemodynamics and the inhibition of secretion of antagonistic factors contribute to the antihypertensive and antihypervolemic action of NPs [Brenner, B. M.; et al., *Physiol Rev* 70 (3): 665-99 (1990)]. In contrast, CNP/NPR-B signaling is mainly involved in tissue remodeling, reproduction and brain functions along with mild hypotensive effects through vasodilation [Chusho, H.; et al., *Proc Natl Acad Sci USA* 98 (7): 4016-21 (2001)]. The residues within the conserved NP ring are necessary for receptor binding while the molecular recognition to specific NPRs are due to subtle differences in their sequences such as C-terminal extensions [Brenner, B. M.; et al., *Physiol Rev* 70 (3): 665-99 (1990)].

The present treatment strategies for HF include the pharmacological intervention of RAAS and SNS activation using angiotensin converting enzyme inhibitors, neprilysin inhibitors, angiotensin receptor inhibitors and diuretics which reduce blood volume and pressure and augment the NP activity and cGMP production as the secondary response [Rogers, C.; Bush, N., *Nurs Clin North Am* 50 (4): 787-99 (2015)]. NPs have a crucial role in restoring the pressure-volume homeostasis through regulation of vascular tone, natriuresis, diuresis and inhibition of RAAS and SNS [Lee, C. Y.; Burnett, J. C., Jr., *Heart Fail Rev* 12 (2): 131-42 (2007)]. Both ANP and BNP levels are elevated in patients with HF, but they fail to exhibit their beneficiary roles due to (a) lower availability of bio-active peptide and (b) lower expression level of the NP receptors [Mukaddam-Daher, S., *Expert Opin Ther Targets* 10 (2): 239-52 (2006)]. Despite their elevation, exogenous infusion of ANP or BNP in HF patients has shown to improve the clinical status of the patients [Lee, C. Y.; Burnett, J. C., Jr., *Heart Fail Rev* 12 (2): 131-42 (2007); Mukaddam-Daher, S., *Expert Opin Ther Targets* 10 (2): 239-52 (2006)]. Despite the beneficiary roles, the exogenous infusion of ANP and BNP has been associated to cause distress due to their diverse physiological actions. Hence, ligands that differentiate the vascular and renal functions of NPs would be of great value to address the personalized needs of various HF patients with distinct imbalances [Strobeck, J. E.; Silver, M. A., *Congest Heart Fail* 10 (2 Suppl 2): 1-6 (2004); Volpe, M.; et al., *Clin Sci (Lond)* 130 (2): 57-77 (2016)].

HF may be broadly classified into: (a) hypertensive HF with euvolemic or mildly hypervolemic, (b) normotensive HF with hypovolemic and (c) hypotensive HF with hypervolemic or hypovolemic states. Natriuretic peptides (NPs) are key hormones which lower blood pressure and volume through their multifaceted actions on blood vessels, kidney, heart and sympathetic nervous system. Infusion of NPs in patients with HF has been beneficial due to their multifaceted action in reducing pressure-volume overload. However, NPs infusion has also been associated with severe hypotension.

New drug leads for the different tensive and volemic states in heart failure are desirable.

SUMMARY OF THE INVENTION

The present invention provides peptides which modulate blood pressure by having vasodilatory and/or diuretic activity.

According to a first aspect, the present invention provides an isolated peptide comprising SEQ ID NO: 1 (CFX$_1$X$_2$X$_3$X$_4$DRIX$_5$X$_6$X$_7$SX$_8$X$_9$GC), wherein X$_1$, X$_2$, X$_8$ each independently comprises any amino acid; X$_3$ comprises R or K; X$_4$ comprises M, I or L; X$_5$ comprises G, S or N; X$_6$ comprises A, H or S, X$_7$ comprises Q, T, S, M or V, and X$_9$ comprises I or L.

According to a second aspect, the present invention provides an isolated peptide according to any aspect of the present invention for use in medicine; for use in therapy; and/or for use as a medicament.

According to a third aspect, the present invention provides the use of at least one isolated peptide according to any aspect of the present invention in the preparation of a medicament for regulating blood pressure-volume and/or for treating a heart condition.

According to a fourth aspect, the present invention provides a method of regulating blood pressure-volume and/or treating a heart condition in a subject comprising administering an effective amount of an isolated peptide according to any according to any aspect of the present invention to the subject.

BRIEF DESCRIPTION OF THE FIGURES

FIG. 1A: Sequence comparison of mammalian and venom NPs. NPs have a canonical 17-membered ring held by a disulphide bond. Residues in pink are conserved among all NPs and residues highlighted in shade are important for NP receptor binding. K-Ring are two key substitutions at position 3 and 14, conserved G residues are replaced by D, and it has a two residue C-terminal tail. Male SD rats were anesthetized with sodium pentobarbital and their femoral artery and vein and urinary bladder was catheterized. Saline with or without the peptide was infused all though the experiment. Shaded region represents the infusion of the peptide. FIG. 1B: Dose-dependent effect of ANP and K-Ring on MAP of anesthetized rats. FIG. 1C: Dose-dependent effects of ANP and K-Ring on urine flow rate in anesthetized rats. The data are represented as mean±SE of five independent experiments.

Control group, 0.2 nmol/kg/min ANP and 2 nmol/kg/min K-Ring profiles are adapted from Sridharan et al., [*Biochem J* 469 (2): 255-66 (2015)].

Figures 2A, 2B, 2C:
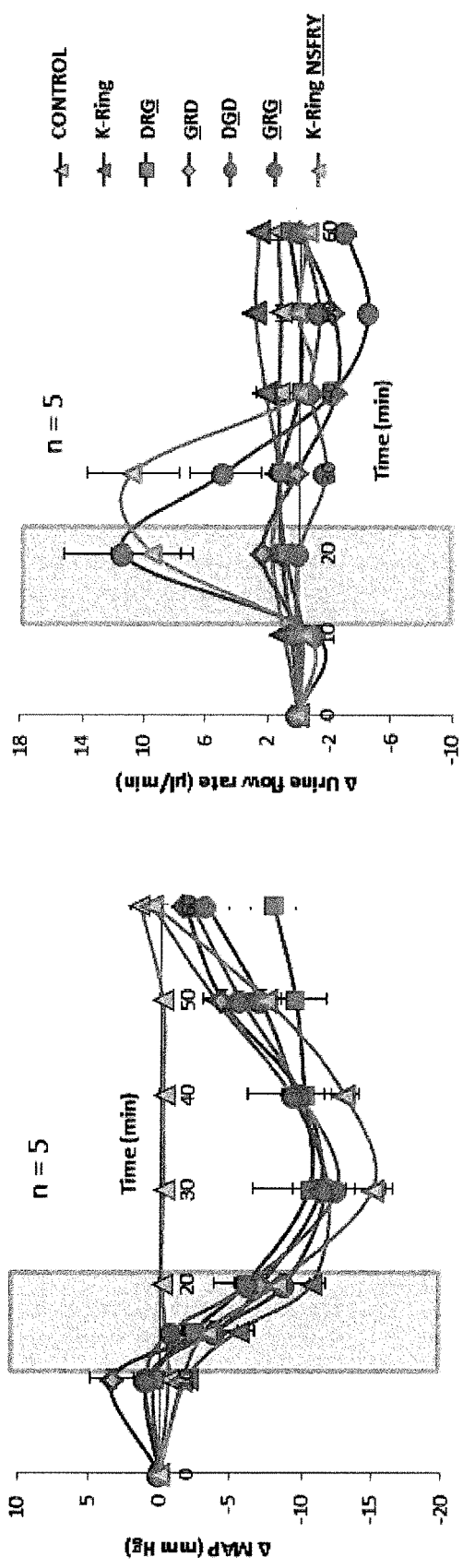

FIGS. 2A-2C show Aspartate residues in the ring and the C-terminal tail are molecular switches that control in-vivo activities of NPs. FIG. 2A: Sequence of K-Ring variants and their in vivo response (Substituted residues are shown in green). Femoral artery, vein and urinary bladder of male SD rats anesthetized with sodium pentobarbital were catheterized to measure hemodynamic and urine volumes in line with the infusion of the peptides. Saline with or without peptide was continuously infused throughout the experiment. Shaded region represents the period of infusion of the peptide. FIG. 2B: Dose-dependent (2 nmol/kg/min) effect of K-Ring and its variants on MAP of anesthetized rats. FIG. 2C: Dose-dependent effects of K-Ring and its variants on urine flow rate in anesthetized rats. The data are represented as mean±SE of five independent experiments.

Control and 2 nmol/kg/min K-Ring profiles have been adapted from Sridharan et al., [*Biochem J* 469 (2): 255-66 (2015)].

FIGS. 3A-3C show incorporation of aspartate and arginine residues in ANP scaffold alters vascular and renal functions. FIG. 3A: Sequence of ANP variants and their in vivo response (Substituted residues are shown in green). Femoral artery, vein and urinary bladder of male SD rats anesthetized with sodium pentobarbital were catheterized to measure hemodynamic and urine volumes in line with the infusion of the peptides. Saline with or without peptide was continuously infused throughout the experiment. Shaded region represents the period of infusion of the peptide. FIG. 3B: Dose-dependent effect of ANP and its variants on MAP of anesthetized rats. FIG. 3C: Dose dependent effects of ANP and its variants on urine flow rate in anesthetized rats. The data are represented as mean±SE of five independent experiments.

Control and 0.2 nmol/kg/min ANP profiles have been adapted from Sridharan et al., [*Biochem J* 469 (2): 255-66 (2015)].

Figure 4A:
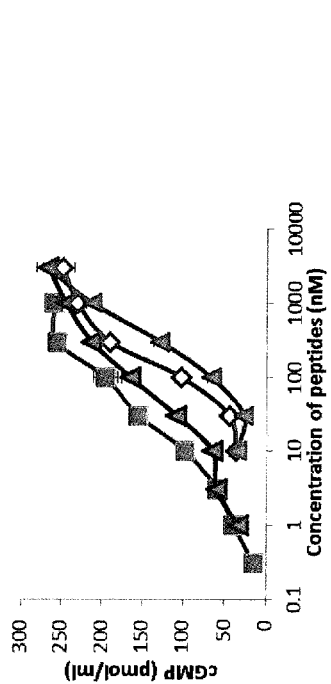
Figure 4B:
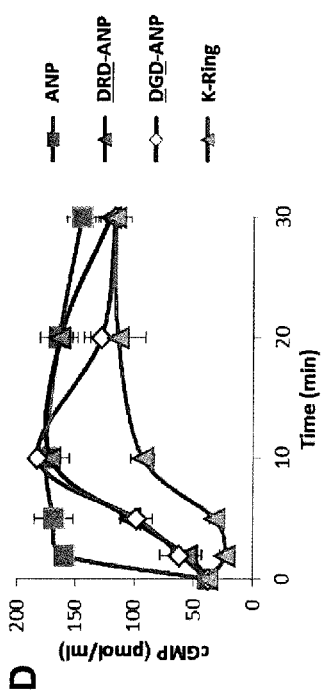
Figure 4C:
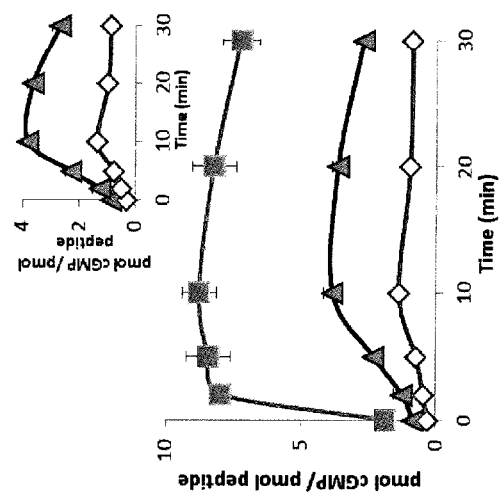
Figure 4D:
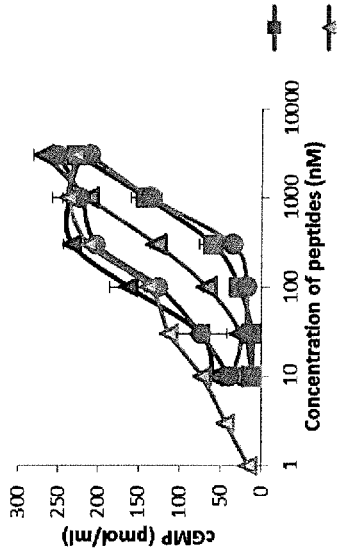
Figure 4E:
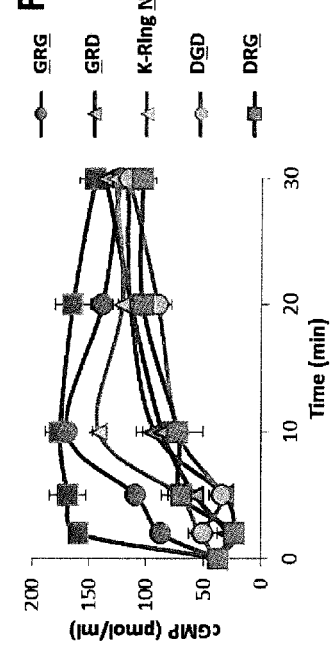
Figure 4F:
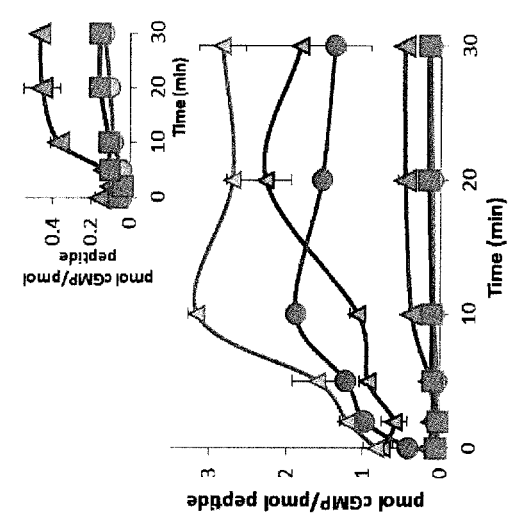

FIGS. 4A-4F show variants of ANP and K-Ring are partial agonists of NPR-A. Amount of cGMP accumulated after the treatment of cells (transiently expressing NPR-A) with NP analogues were determined. FIGS. 4A, 4B: Dose-response of cGMP production after 30 min treatment with ANP, K-Ring and their variants. FIGS. 4C, 4D: Activation kinetics of NPR-A measured through time-chase study using EC 50 concentration of peptides. FIGS. 4E, 4F: Activation kinetics of NPR-A per pmole of NPs. The data are represented as mean±SE of three independent experiments.

Figure 5:
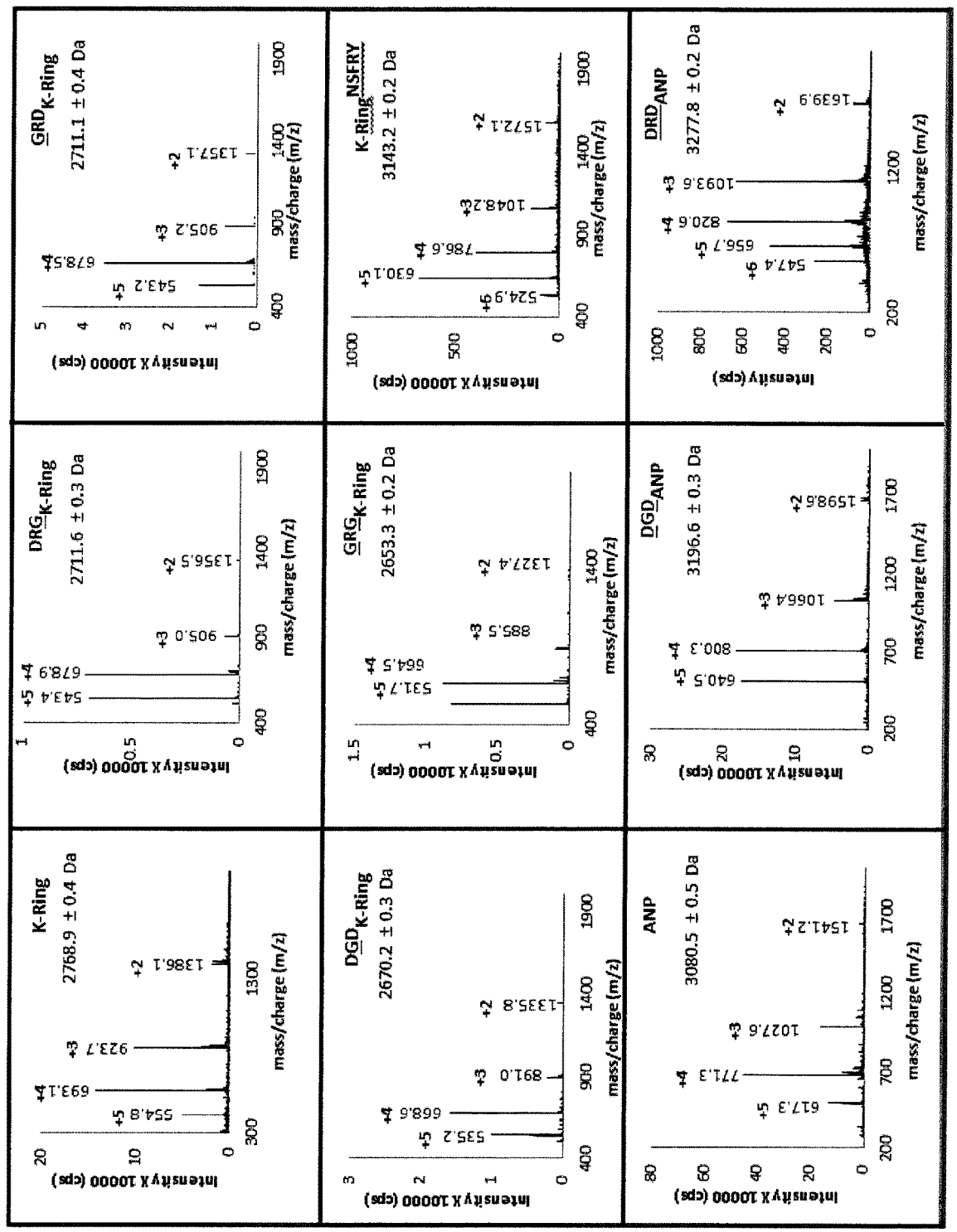

FIG. 5 shows molecular mass and homogeneity of ANP, K-Ring and their variants. Synthetic ANP, K-Ring and their variants were synthesized using Fmoc-based solid phase peptide chemistry and purified by reversed-phase HPLC. The purified peptides were oxidized using 10% DMSO solution under alkaline conditions and purified HPLC. The mass of the purified, oxidized peptides were analyzed by ESI-Ion trap MS. Calculated masses of peptides are shown.

FIGS. 6A-6D show changes in vascular parameters in response to dose dependent infusion of ANP and K-Ring. Femoral artery, vein and urinary bladder were catheterized in male SD rats anesthetized using sodium pentobarbital. Saline with or without the peptides was infused continuously until the end of experiment. Shaded region represents the fusion of peptide. FIG. 6A: Heart rate, FIG. 6B: Pulse pressure, FIG. 6C: Systolic pressure, FIG. 6D: Diastolic pressure changes associated with infusion of two different doses of ANP and K-Ring.

FIGS. 7A-7D show changes in vascular parameters in response to dose dependent infusion of K-Ring variants. Femoral artery, vein and urinary bladder were catheterized in male SD rats anesthetized using sodium pentobarbital. Saline with or without the peptides was infused continuously until the end of experiment. Shaded region represents the fusion of peptide. FIG. 7A: Heart rate, FIG. 7B: Pulse pressure, FIG. 7C: Systolic pressure, FIG. 7D: Diastolic pressure changes associated with infusion of K-Ring variants.

Data shown are an average of five independent trails and represented as mean±SE. Control and 2 nmol/kg/min K-Ring profiles have been adapted from Sridharan et al., [*Biochem J* 469 (2): 255-66 (2015)].

FIGS. 8A-8D show changes in vascular parameters in response to dose dependent infusion of ANP variants.

Figure 8A:
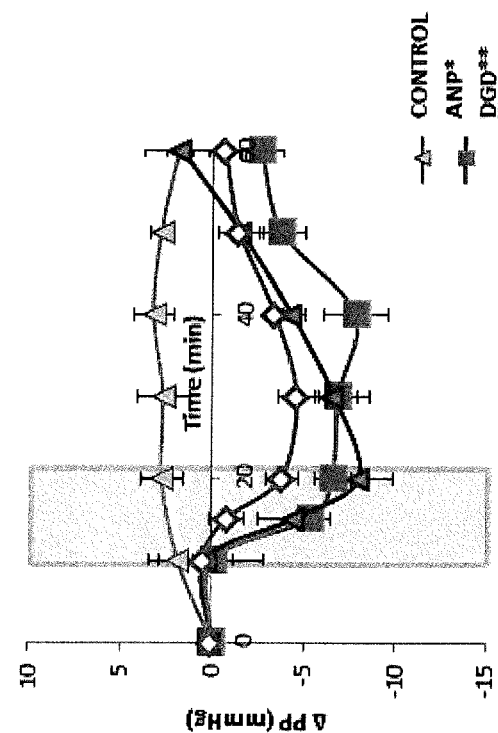
Figure 8B:
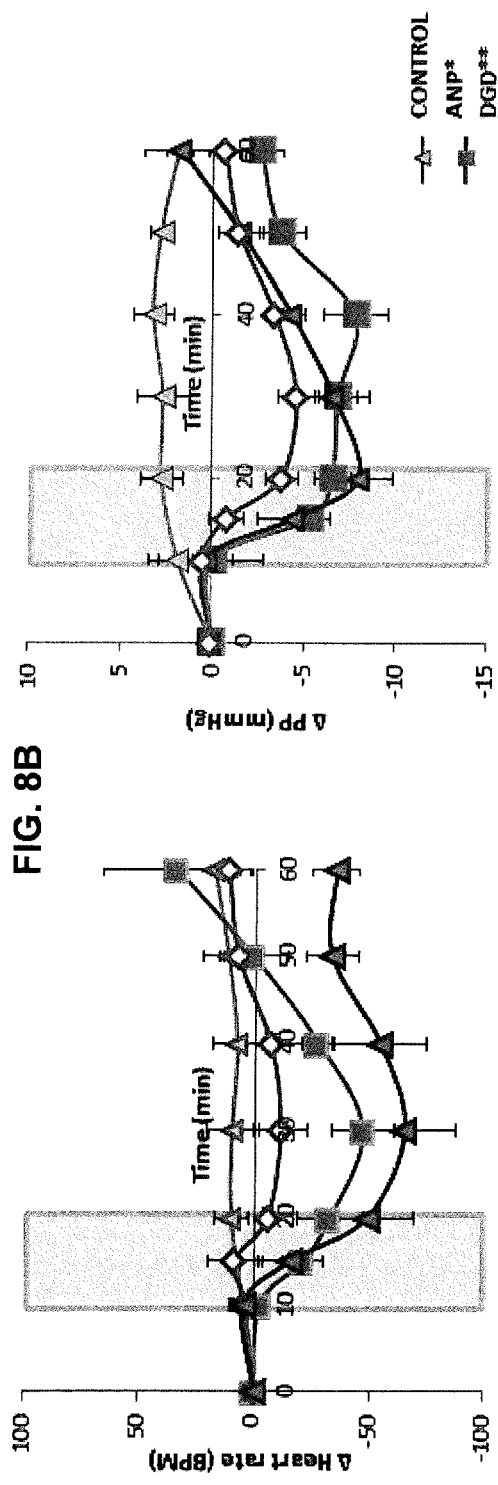
Figure 8C:
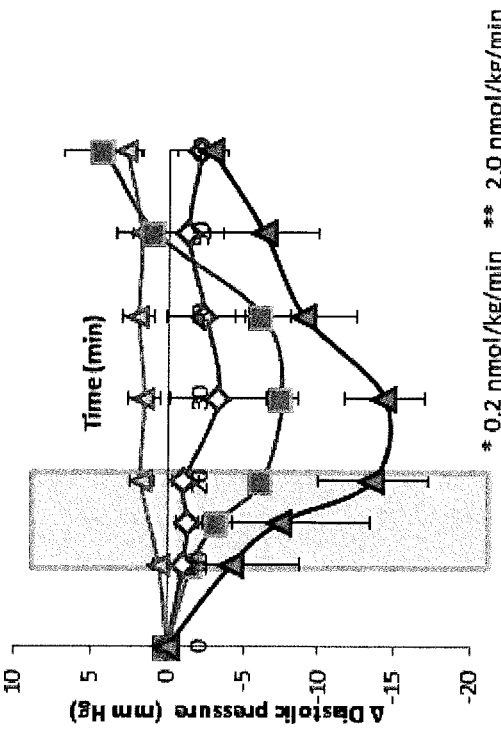
Figure 8D:
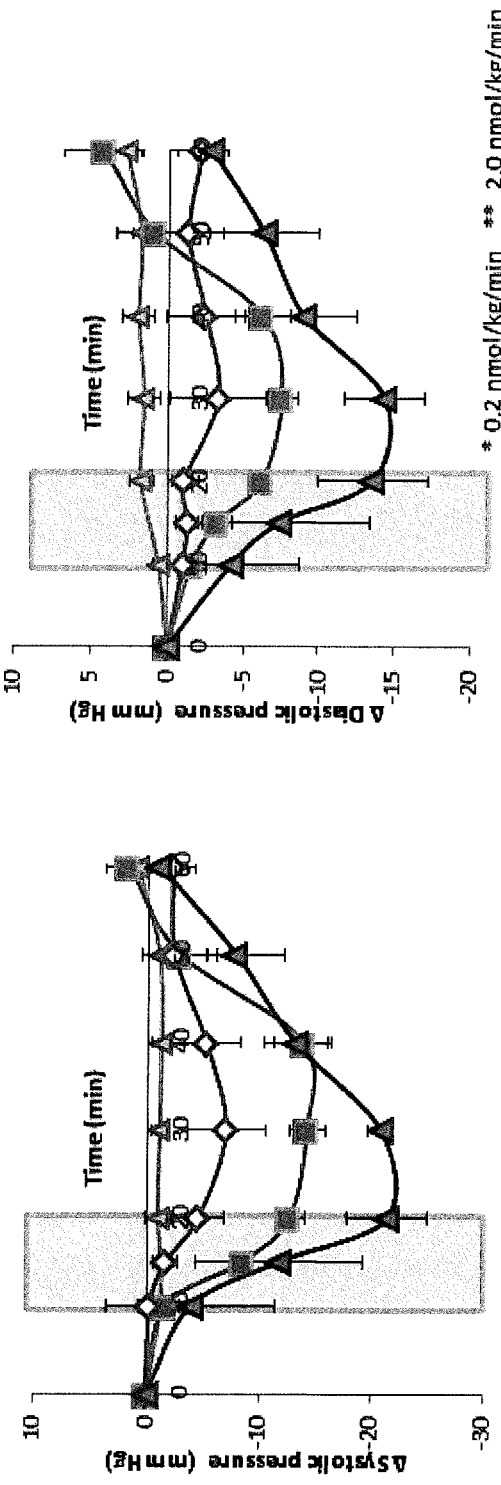

Femoral artery, vein and urinary bladder were catheterized in male SD rats anesthetized using sodium pentobarbital. Saline with or without the peptides was infused continuously until the end of experiment. Shaded region represents the fusion of peptide. FIG. 8A: Heart rate, FIG. 8B: Pulse pressure, FIG. 8C: Systolic pressure, FIG. 8D: Diastolic pressure changes associated with infusion of ANP variants.

Data shown are an average of five independent trails and represented as mean±SE. Control group, 0.2 nmol/kg/min ANP and 2 nmol/kg/min K-Ring profiles are adapted from Sridharan et al., [*Biochem J* 469 (2): 255-66 (2015)].

DEFINITIONS

Certain terms employed in the specification, examples and appended claims are collected here for convenience.

The term "amino acid sequence," as used herein, refers to an oligopeptide, peptide, polypeptide, or protein sequence, or a fragment of any of these, and to naturally occurring or synthetic molecules.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, an amino acid residue that is substituted at position 2, 3 and/or 14 of the 17-residue ring of the natriuretic peptide to effect a change in peptide activity could itself be replaced by a similar amino acid without significantly altering the activity. For example, if D (Asp) is substituted into the 17-residue ring of the natriuretic peptide to effect a change in peptide activity, it could be replaced with another amino acid residue from the same (acidic residue) side chain family such as E (Glu). Likewise, K (Lys) could be used instead of R (Arg), as both are basic residues. Moreover, the C-terminal NSFRY (SEQ ID NO: 57) is known to interact with the receptor. Amino acid Q (Gln) is equivalent to N (Asn) (both hydrophilic, neutral residues), T (Thr) is equivalent to S (Ser) (both hydrophilic, neutral residues with hydroxyl side chains), and Y (Tyr) and W (Trp) are equivalent to F (Phe) (both hydrophobic, aromatic residues). Permutations of these residues may also help in modifying the C-terminal tail.

A "composition comprising a given polynucleotide sequence" or a "composition comprising a given amino acid sequence," as these terms are used herein, refer broadly to any composition containing the given polynucleotide or amino acid sequence of the invention. The composition may comprise a dry formulation or an aqueous solution.

The phrases "nucleic acid" or "nucleic acid sequence," as used herein, refer to an oligonucleotide, nucleotide, polynucleotide, or any fragment thereof, to DNA or RNA of genomic or synthetic origin which may be single-stranded or double-stranded and may represent the sense or the antisense strand, to peptide nucleic acid (PNA), or to any DNA-like or RNA-like material.

The term "subject" is herein defined as vertebrate, particularly mammal, more particularly human. For purposes of research, the subject may particularly be at least one animal model, e.g., a mouse, rat and the like. In particular, for treatment or prophylaxis of blood pressure-related diseases, the subject may be a human.

The term "treatment", as used in the context of the invention refers to ameliorating, therapeutic or curative treatment.

As used herein, the term "comprising" or "including" is to be interpreted as specifying the presence of the stated features, integers, steps or components as referred to, but does not preclude the presence or addition of one or more features, integers, steps or components, or groups thereof. However, in context with the present disclosure, the term "comprising" or "including" also includes "consisting of". The variations of the word "comprising", such as "comprise" and "comprises", and "including", such as "include" and "includes", have correspondingly varied meanings.

DETAILED DESCRIPTION OF THE INVENTION

Bibliographic references mentioned in the present specification are for convenience listed in the form of a list of references and added at the end of the examples.

The present invention provides an isolated peptide comprising SEQ ID NO: 1 ($CFX_1X_2X_3X_4DRIX_5X_6X_7SX_8X_9GC$), wherein $X_1$, $X_2$, $X_8$ each independently comprises any amino acid; $X_3$ comprises R or K; $X_4$ comprises M, I or L; $X_5$ comprises G, S or N; $X_6$ comprises A, H or S, $X_7$ comprises Q, T, S, M or V, and $X_9$ comprises I or L.

In one preferred embodiment, the isolated peptides and/or nucleic acid of the invention exclude a naturally occurring peptide and/or a nucleic acid molecule, unless they are modified in some way by standard methods known in the art for the purpose of, for example, increasing their stability in vivo and/or in vitro.

In another preferred embodiment, an isolated cDNA molecule which replicates a naturally occurring sequence of exons encoding naturally occurring peptide is also excluded from the present invention.

Examples of naturally occurring peptides are:

Atrial natriuretic peptide (ANP) with sequence:

```
                                        (SEQ ID NO: 52)
          SLRRSSCFGGRMDRIGAQSGLGCNSFRY
```

Krait venom natriuretic peptide (KNP) with sequence:

```
                                        (SEQ ID NO: 53)
GLLISCFDRRIDRISHTSDIGCRHRKDPPRAPPAAPSAAPLAVTWLIRDL
RADSKQSRAA
```

B-type natriuretic peptide (BNP) with sequence:

```
                                        (SEQ ID NO: 54)
          SPKMVQGSGCFGRKMDRISSSSGLGCKVLRRH
```

C-type natriuretic peptide (CNP) with sequence:

GLSKGCFGLKLDRIGSMSGLGC (SEQ ID NO: 55)

*Dendroaspis* natriuretic peptide (DNP) with sequence:

EVKYDPCFGHKIDRINHVSNLGCPSLRDPRPNAPSTSA (SEQ ID NO: 56)

Any use of a cDNA molecule; a naturally occurring peptide and/or a naturally occurring nucleic acid molecule will be regarded as part of the present invention.

It will be appreciated that the present invention includes an isolated peptide comprising or consisting of a sequence of the 17-residue ring of a natriuretic peptide.

It will be appreciated that the present invention also includes an isolated peptide comprising a sequence of the 17-residue ring of a natriuretic peptide comprising at least one modified amino acid at positions 2, 3 and/or 14 of the 17-residue ring of the natriuretic peptide. By "modified" the term is intended to include substitution of one amino acid by another in the 17-residue ring of a natriuretic peptide. For example, amino acid G (Gly) may replace amino acid D (Asp) at position 2.

It will be further appreciated that the present invention includes an isolated full-length natriuretic peptide comprising at least one modified amino acid at positions 2, 3 and/or 14 of its 17-residue ring. Moreover, it would be understood that an amino acid substitution made at the position 2, 3 and/or 14 could be replaced by a conservative amino acid. For example, if R (Arg) is substituted into position 3 another similar (conservative) amino acid could replicate the effect of the R on peptide activity; such as substitution with K (Lys).

The present invention is further described by the following embodiments of invention.

According to a first aspect, the present invention provides an isolated peptide having vasodilatory and/or diuretic activity in mammals, comprising the amino acid sequence SEQ ID NO: 1 (CFX$_1$X$_2$X$_3$X$_4$DRIX$_5$X$_6$X$_7$SX$_8$X$_9$GC), wherein X$_1$, X$_2$, X$_8$ each independently comprises any amino acid; X$_3$ comprises R or K; X$_4$ comprises M, I or L; X$_5$ comprises G, S or N; X$_6$ comprises A, H or S, X$_7$ comprises Q, T, S, M or V; and X$_9$ comprises I or L, wherein the peptide does not consist of the amino acid sequence depicted by SEQ ID NO: 52, SEQ ID NO: 53, SEQ ID NO: 54, SEQ ID NO: 55 or SEQ ID NO: 56.

According to a preferred embodiment the isolated peptide according to the first aspect comprises SEQ ID NO: 2 (CFX$_1$X$_2$X$_3$X$_4$DRIX$_5$X$_6$X$_7$SX$_8$X$_9$GC) wherein X$_1$ comprises D or G. X$_1$ could comprise E instead of D.

According to another preferred embodiment the isolated peptide according to the first aspect comprises SEQ ID NO: 3 (CFX$_1$X$_2$X$_3$X$_4$DRIX$_5$X$_6$X$_7$SX$_8$X$_9$GC) wherein X$_2$ comprises R or G. X$_2$ could comprise K instead of R.

According to another preferred embodiment the isolated peptide according to the first aspect comprises SEQ ID NO: 4 (CFX$_1$X$_2$X$_3$X$_4$DRIX$_5$X$_6$X$_7$SX$_8$X$_9$GC), wherein X$_8$ comprises D or G. X$_8$ could comprise E instead of D.

According to another preferred embodiment the isolated peptide according to the first aspect or first preferred embodiment comprises SEQ ID NO: 5 (CFDX$_2$X$_3$X$_4$DRIX$_5$X$_6$X$_7$SX$_8$X$_9$GC).

According to another preferred embodiment the isolated peptide according to the first aspect or first preferred embodiment comprises SEQ ID NO: 6 (CFGX$_2$X$_3$X$_4$DRIX$_5$X$_6$X$_7$SX$_8$X$_9$GC).

According to another preferred embodiment the isolated peptide according to the first aspect or second preferred embodiment comprises SEQ ID NO: 7 (CFX$_1$RX$_3$X$_4$DRIX$_5$X$_6$X$_7$SX$_8$X$_9$GC).

According to another preferred embodiment the isolated peptide according to the first aspect or second preferred embodiment comprises SEQ ID NO: 8 (CFX$_1$GX$_3$X$_4$DRIX$_5$X$_6$X$_7$SX$_8$X$_9$GC).

According to another preferred embodiment the isolated peptide according to the first aspect or third preferred embodiment comprises SEQ ID NO: 9 (CFX$_1$X$_2$X$_3$X$_4$DRIX$_5$X$_6$X$_7$SDX$_9$GC).

According to another preferred embodiment the isolated peptide according to the first aspect or third preferred embodiment comprises SEQ ID NO: 10 (CFX$_1$X$_2$X$_3$X$_4$DRIX$_5$X$_6$X$_7$SGX$_9$GC).

According to another preferred embodiment the isolated peptide according to the first aspect comprises SEQ ID NO: 11 (CFDRX$_3$X$_4$DRIX$_5$X$_6$X$_7$SX$_8$X$_9$GC).

According to another preferred embodiment the isolated peptide according to the first aspect comprises SEQ ID NO: 12 (CFGRX$_3$X$_4$DRIX$_5$X$_6$X$_7$SX$_8$X$_9$GC).

According to another preferred embodiment the isolated peptide according to the first aspect comprises SEQ ID NO: 13 (CFDGX$_3$X$_4$DRIX$_5$X$_6$X$_7$SX$_8$X$_9$GC).

According to another preferred embodiment the isolated peptide according to the first aspect comprises SEQ ID NO: 14 (CFGGX$_3$X$_4$DRIX$_5$X$_6$X$_7$SX$_8$X$_9$GC).

According to another preferred embodiment the isolated peptide according to the first aspect comprises SEQ ID NO: 15 (CFDX$_2$X$_3$X$_4$DRIX$_5$X$_6$X$_7$SDX$_9$GC).

According to another preferred embodiment the isolated peptide according to the first aspect comprises SEQ ID NO: 16 (CFGX$_2$X$_3$X$_4$DRIX$_5$X$_6$X$_7$SDX$_9$GC).

According to another preferred embodiment the isolated peptide according to the first aspect comprises SEQ ID NO: 17 (CFDX$_2$X$_3$X$_4$DRIX$_5$X$_6$X$_7$SGX$_9$GC).

According to another preferred embodiment the isolated peptide according to the first aspect comprises SEQ ID NO: 18 (CFGX$_2$X$_3$X$_4$DRIX$_5$X$_6$X$_7$SGX$_9$GC).

According to another preferred embodiment the isolated peptide according to the first aspect comprises SEQ ID NO: 19 (CFX$_1$RX$_3$X$_4$DRIX$_5$X$_6$X$_7$SDX$_9$GC).

According to another preferred embodiment the isolated peptide according to the first aspect comprises SEQ ID NO: 20 (CFX$_1$R X$_3$X$_4$DRIX$_5$X$_6$X$_7$SGX$_9$GC).

According to another preferred embodiment the isolated peptide according to the first aspect comprises SEQ ID NO: 21 (CFX$_1$G X$_3$X$_4$DRIX$_5$X$_6$X$_7$SDX$_9$GC).

According to another preferred embodiment the isolated peptide according to the first aspect comprises SEQ ID NO: 22 (CFX$_1$G X$_3$X$_4$DRIX$_5$X$_6$X$_7$SGX$_9$GC).

According to another preferred embodiment the isolated peptide according to the first aspect comprises SEQ ID NO: 1, wherein X$_1$ is G or D, X$_2$ is G or R and X$_8$ is G or D.

According to another preferred embodiment the isolated peptide according to the first aspect comprises SEQ ID NO: 1, wherein X$_1$, X$_2$ and X$_5$ are selected from, respectively, G, R and D; D, R and G; D, G and D; and D, R and D.

According to another preferred embodiment the isolated peptide according to the first aspect comprises SEQ ID NO: 23 (CFX$_1$X$_2$X$_3$X$_4$DRIX$_5$X$_6$X$_7$SX$_8$X$_9$GCNSFRY). It would be understood that within the NSFRY (SEQ ID NO: 57) tail the amino acid N is equivalent to Q (both hydrophilic, neutral residues), S is equivalent to T (both hydrophilic, neutral residues with hydroxyl side chains), and F is equivalent to W and Y (both hydrophobic, aromatic residues). Substitution with these conservative residues should not significantly change the activity of the C-terminal tail.

According to another preferred embodiment the isolated peptide according to the first aspect comprises a sequence selected from the group consisting of:

(CFDRRIDRISHTSDIGC); SEQ ID NO: 24

(CFGRRIDRISHTSDIGC); SEQ ID NO: 25

(CFDGRIDRISHTSDIGC); SEQ ID NO: 26

(CFDRRIDRISHTSGIGC); SEQ ID NO: 27

(CFGGRIDRISHTSDIGC); SEQ ID NO: 28

(CFGRRIDRISHTSGIGC); SEQ ID NO: 29

(CFDGRIDRISHTSGIGC); SEQ ID NO: 30
and (CFGGRIDRISHTSGIGC). SEQ ID NO: 31

According to another preferred embodiment the isolated peptide according to the first aspect is selected from the group consisting of:

(GLLISCFDRRIDRISHTSDIGCRH); SEQ ID NO: 32

(GLLISCFDRRIDRISHTSGIGCRH); SEQ ID NO: 33

(GLLISCFGRRIDRISHTSDIGCRH); SEQ ID NO: 34

(GLLISCFDGRIDRISHTSDIGCRH); SEQ ID NO: 35

(GLLISCFGRRIDRISHTSGIGCRH); SEQ ID NO: 36

(GLLISCFDRRIDRISHTSDIGCNSFRY); SEQ ID NO: 37

(GLLISCFGRRIDRISHTSDIGCRHRKDPPRAPPAAPSAAPLAVTWLIRD LRADSKQSRAA); SEQ ID NO: 38

(GLLISCFDGRIDRISHTSDIGCRHRKDPPRAPPAAPSAAPLAVTWLIRD LRADSKQSRAA); SEQ ID NO: 39

(GLLISCFDRRIDRISHTSGIGCRHRKDPPRAPPAAPSAAPLAVTWLIRD LRADSKQSRAA); SEQ ID NO: 40

(GLLISCFGGRIDRISHTSDIGCRHRKDPPRAPPAAPSAAPLAVTWLIRD LRADSKQSRAA); SEQ ID NO: 41

(GLLISCFGRRIDRISHTSGIGCRHRKDPPRAPPAAPSAAPLAVTWLIRD LRADSKQSRAA); SEQ ID NO: 42

(GLLISCFDGRIDRISHTSGIGCRHRKDPPRAPPAAPSAAPLAVTWLIRD LRADSKQSRAA); SEQ ID NO: 43
and (GLLISCFGGRIDRISHTSGIGCRHRKDPPRAPPAAPSAAPLAVTWLIRD LRADSKQSRAA). SEQ ID NO: 44

According to another preferred embodiment the isolated peptide according to the first aspect is selected from the group consisting of:

(SLRRSSCFDGRMERIGAQSGLGCNSFRY); SEQ ID NO: 45

(SLRRSSCFGRRMDRIGAQSGLGCNSFRY); SEQ ID NO: 46

(SLRRSSCFGGRMDRIGAQSDLGCNSFRY); SEQ ID NO: 47

(SLRRSSCFDRRMDRIGAQSGLGCNSFRY); SEQ ID NO: 48

(SLRRSSCFDGRMDRIGAQSDLGCNSFRY); SEQ ID NO: 49

(SLRRSSCFGRRMDRIGAQSDLGCNSFRY); SEQ ID NO: 50
and (SLRRSSCFDRRMDRIGAQSDLGCNSFRY). SEQ ID NO: 51

According to another preferred embodiment there is provided an isolated peptide according to the first aspect, wherein when X1 is G and X8 is G, or when NSFRY (SEQ ID NO: 57) is present at the C-terminal end of the peptide, diuretic activity of the peptide is elicited.

According to another preferred embodiment there is provided an isolated peptide according to the first aspect, wherein a) when X1 is G the peptide elicits reduced heart rate and pulse pressure compared to when X1 is D;

b) when X2 is G the peptide elicits exclusive diuresis at low dose and hypotension along with diuresis at higher dose;

c) when X2 is R the peptide elicits a reversed preference of pharmacological activity to that shown in b);

d) when X8 is G the peptide elicits sustained vasodilatory effects compared to when X8 is D; and e) when X1 is D and X8 is D the peptide elicits exclusive hypotension without significant diuresis.

In a preferred embodiment of the invention there is provided an isolated peptide having vasodilatory and/or diuretic functions. Preferably, the isolated peptide has an amino acid sequence according to any one of SEQ ID NO: 1 to SEQ ID NO: 51.

According to another preferred embodiment there is provided an isolated peptide according to the first aspect, wherein peptides from the group comprising SEQ ID NO: 25, SEQ ID NO: 26, SEQ ID NO: 27, SEQ ID NO: 33, SEQ ID NO: 34, SEQ ID NO: 35 and SEQ ID NO: 51 have vasodilatory activity; peptides from the group comprising SEQ ID NO: 29, SEQ ID NO: 36 and SEQ ID NO: 37 have vasodilatory and diuretic activity; and peptides from the group comprising SEQ ID NO: 49, have renal activity.

The invention includes an isolated peptide as disclosed herein for use in medicine; for use in therapy; and/or for use as a medicament. For example, the invention includes an isolated peptide as disclosed herein for use in regulating blood pressure-volume (for example in high blood pressure or low blood pressure) and/or diuresis. The invention also includes an isolated peptide as disclosed herein for use in treating a heart condition (for example heart failure).

According to a second aspect, the present invention provides an isolated peptide according to any aspect of the present invention for use in medicine; for use in therapy; and/or for use as a medicament.

The invention includes the use of at least one isolated peptide as disclosed herein in the preparation of a medicament for regulating blood pressure-volume (for example in high blood pressure or low blood pressure) and/or diuresis. The invention also includes the use of at least one isolated peptide as disclosed herein in the preparation of a medicament for treating a heart condition (for example heart failure).

According to a third aspect, the present invention provides the use of at least one isolated peptide according to any aspect of the present invention in the preparation of a medicament for regulating blood pressure-volume and/or for treating a heart condition.

The invention includes a method of regulating blood pressure-volume (for example in high blood pressure or low blood pressure) in a subject comprising administering an effective amount of an isolated peptide as disclosed herein to the subject. The invention includes a method of treating a heart condition (for example heart failure) in a subject comprising administering an effective amount of an isolated peptide as disclosed herein to the subject.

According to a fourth aspect, the present invention provides a method of regulating blood pressure-volume and/or treating a heart condition in a subject comprising administering an effective amount of an isolated peptide according to any according to any aspect of the present invention to the subject.

The pure vasodilator agents of the invention (such as DRG-K-Ring, GRD-K-Ring, DGD-K-Ring; SEQ ID NOs: 33-35) and DRD-ANP (SEQ ID NO: 51) may be used to help in "warm" and minimally "wet" patients in whom the need is to redistribute blood volume from the heart and thorax to the periphery and to avoid major volume depletion. These patients have well preserved BP and do not have extreme volume expansion and can tolerate reductions in BP.

The diuretic only agents of the invention (such as DGD-ANP; SEQ ID NO: 49) would be applied in volume expanded (edematous) patients with excess fluid in both lungs and periphery but low blood pressure. This "wet and cold" subgroup is very difficult to treat as there is a need to excrete excess volume (sodium and water) whilst avoiding further reductions in BP which may precipitate worsening shock complicated by renal failure.

Compounds of the present invention will generally be administered as a pharmaceutical formulation in admixture with a pharmaceutically acceptable adjuvant, diluent or carrier, which may be selected with due regard to the intended route of administration and standard pharmaceutical practice. Such pharmaceutically acceptable carriers may be chemically inert to the active compounds and may have no detrimental side effects or toxicity under the conditions of use. Suitable pharmaceutical formulations may be found in, for example, Remington *The Science and Practice of Pharmacy,* 19th ed., Mack Printing Company, Easton, Pa. (1995). For parenteral administration, a parenterally acceptable aqueous solution may be employed, which is pyrogen free and has requisite pH, isotonicity, and stability. Suitable solutions will be well known to the skilled person, with numerous methods being described in the literature. A brief review of methods of drug delivery may also be found in e.g. Langer, *Science* (1990) 249, 1527.

Otherwise, the preparation of suitable formulations may be achieved routinely by the skilled person using routine techniques and/or in accordance with standard and/or accepted pharmaceutical practice.

The amount of a compound in any pharmaceutical formulation used in accordance with the present invention will depend on various factors, such as the severity of the condition to be treated, the particular patient to be treated, as well as the compound(s) which is/are employed. In any event, the amount of a compound in the formulation may be determined routinely by the skilled person.

For example, a solid oral composition such as a tablet or capsule may contain from 1 to 99% (w/w) active ingredient; from 0 to 99% (w/w) diluent or filler; from 0 to 20% (w/w) of a disintegrant; from 0 to 5% (w/w) of a lubricant; from 0 to 5% (w/w) of a flow aid; from 0 to 50% (w/w) of a granulating agent or binder; from 0 to 5% (w/w) of an antioxidant; and from 0 to 5% (w/w) of a pigment. A controlled release tablet may in addition contain from 0 to 90% (w/w) of a release-controlling polymer.

A parenteral formulation (such as a solution or suspension for injection or a solution for infusion) may contain from 1 to 50% (w/w) active ingredient; and from 50% (w/w) to 99% (w/w) of a liquid or semisolid carrier or vehicle (e.g. a solvent such as water); and 0-20% (w/w) of one or more other excipients such as buffering agents, antioxidants, suspension stabilisers, tonicity adjusting agents and preservatives.

Depending on the disorder, and the patient, to be treated, as well as the route of administration, compounds may be administered at varying therapeutically effective doses to a patient in need thereof.

However, the dose administered to a mammal, particularly a human, in the context of the present invention should be sufficient to effect a therapeutic response in the mammal over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the potency of the specific compound, the age, condition, body weight, sex and response of the patient to be treated, and the stage/severity of the disease.

Accordingly, in a preferred embodiment the invention includes any composition containing the given polynucleotide or amino acid sequence of the invention.

The invention also includes an isolated nucleic acid molecule encoding an isolated peptide as disclosed herein.

According to a fifth aspect, the present invention provides an isolated nucleic acid molecule or polynucleotide encoding an isolated peptide according to any aspect of the present invention. Preferably the nucleic acid molecule or polynucleotide is comprised within an expression construct to produce peptides of the invention.

Having now generally described the invention, the same will be more readily understood through reference to the following examples which are provided by way of illustration, and are not intended to be limiting of the present invention.

EXAMPLES

Standard molecular biology techniques known in the art and not specifically described were generally followed as described in Green and Sambrook, Molecular Cloning: A Laboratory Manual, Cold Springs Harbor Laboratory, New York (2012).

Example 1

Materials and Methods
Synthesis and Purification of ANP, K-Ring and Variants

All peptides were synthesized using manual Fmoc-based peptide synthesis. ANP and variants were synthesized using Tyr-preloaded Wang resin while K-Ring and variants were synthesized using Novasyn TGR resin. The methodology adopted for synthesis, purification and folding are as described in Sridharan et al., [*Biochem J* 469 (2): 255-66 (2015)].

Animals

Male Sprague-Dawley (SD) rats (220-280 g) were obtained from Invivos, Singapore. Animals were acclimatized in the Animal Holding unit, NUS for 3 days before the experiment. The experiments were conducted under the guidance and approval of Institutional Animal Care and Use Committee, NUS (041/12).

In-Vivo Activity Assay

The experiments were performed as described in Sridharan et al., [*Biochem J* 469 (2): 255-66 (2015)]. In brief, animals were anesthetized with sodium pentobarbital (60-70 mg/kg) and catheters were inserted in femoral artery, vein and urinary bladder. The body temperature of the animals was maintained using a thermostatic heat pad at 37° C. Continuous infusions (2 ml/h) of 0.2% BSA saline (with or without peptide) was administered through the femoral vein while a pressure transducer attached to the femoral artery recorded on-line changes in mean arterial pressure (MAP), heart rate (HR) and pulse pressure (PP). Urine was collected and the volume was measured after every 10 min. Experiments encompassed control (2×10 min), experimental (1×10 min) and recovery (4×10 min) periods. All animals were euthanized at the end of the experiment in carbon-di-oxide chambers.

Cell Culture and Transfection

The experiments were performed as described in Sridharan et al., [*Biochem J* 469 (2): 255-66 (2015)]. Dulbecco's modified Eagle's medium supplemented with 10% fetal bovine serum, 100 U/ml penicillin and 100 µg/ml streptomycin and 2 mM glutamine was used to grow CHO-K1 cells in a humidified incubator at 37° C. with 5% $CO_2$. The cells were maintained by sub-culturing using 0.5% trypsin every three days. Cells (1×10$^5$) were seeded per well in 24-well plate and grown for 16 h. Cells in each well were transfected with 0.8 µg of plasmid encoding rat NPR-A using 2 µl of Lipofectamine™ 2000 transfection reagent. Cells were treated with the peptides 24 h after transfection.

Whole Cell cGMP Assay

NPR-A transfected CHO-K1 cells were treated with varying concentrations of peptides (10 nM to 10 µM dissolved in basal media containing 0.5 mM IBMX) for 30 min. The end-point accumulation of cGMP was measured after cell-lysis with 200 µl of 0.1 N HCl using Enzo life sciences cGMP ELISA kit (manufacturer's protocol).

Time-chase study was performed by treating the cells with $EC_{50}$ concentration of the peptides. The reactions were terminated at the indicated time-points (0, 2, 5, 10, 20 and 30 min) by treating the cells with 0.1 N HCl. The cGMP concentration in the cell lysate was measured using cGMP ELISA kit (Enzo life sciences).

Statistical Analysis

The data are represented as mean±SEM. Statistical analysis was performed using one way-ANOVA using two-tailed t-test. A p-value <0.5 was considered significant.

Example 2

Functional Switches in K-Ring Responsible for Hemodynamic Effects

To understand the role of unusual substitutions within K-Ring and the C-terminal tail, we evaluated pharmacological activities of several mutants. The first generation of single mutants included substitution of D3, R4 and D14 with G (FIG. 2A) within K-Ring. These single point mutants, $^{GRD}$K-Ring, $^{DGD}$K-Ring and $^{DRG}$K-Ring (the 'mutated' residues are underlined), were synthesized (FIG. 5, Table 3) and their in-vivo activities were evaluated in anesthetized rats (FIGS. 2B, 2C). Infusion of 2 nmol/kg/min of all the three single mutants induced similar drop in MAP (≈12 mmHg) without any significant change in urine volume (FIGS. 2B, 2C, Table 1) as K-Ring. $^{GRD}$K-Ring evoked a greater drop on heart rate (HR) (−44.8±20.2 BPM) compared to K-Ring (−22.2±12.1 BPM), which was similar to that of 0.2 nmol/kg/min infusion of ANP (−47.0±13.5 BPM) (FIGS. 6A, 6B, Table 1). Further this peptide also elicited greater reduction in pulse pressure (PP) (−11.5±2.3 mmHg) compared to both K-Ring (−4.5±1.7 mmHg) and ANP (−7.7±3.9 mmHg) (FIGS. 5A, 5B, 6A, 6B, Table 1). $^{DGD}$K-Ring infusion resulted in similar HR and PP changes (−21.8±9.5 BPM, −5.8±0.97 mmHg) as K-Ring (Table 1). This mutant showed a slower initial decrease in BP and HR as the peptide was infused (FIGS. 6A, 6B). $^{DRG}$K-Ring infusion, although showed similar vascular response (HR: −18.1±3.1 BPM and PP: −3.2±3.0 mmHg) like K-Ring (Table 1), but the changes in MAP and HR did not recover back to the baseline within the experimental period (FIGS. 2B, 6A, 6B). Subsequently, we synthesized a double mutant, $^{GRG}$K-Ring, in which both D residues were substituted by G. This peptide elicited similar changes in MAP, HR and urine flow rate (MAP: −11.8±1.5 mmHg, HR: −39.1±11.5 BPM 11.4±3.8 µl/min). Despite the similar responses to ANP, $^{GRG}$K-Ring showed greater influence on PP (−12.9±0.7 mmHg) like $^{GRD}$K-Ring (FIGS. 2, 6A, 6B). Thus, the results indicated that the D3G substitution led to a higher drop in HR and PP, for similar changes in MAP while D14G substitution delayed the recovery of MAP and HR. Interestingly, substitution of both D3 and D14 by G introduces renal activity in K-Ring peptides. Thus, both D3 and D14 residues act as the control switches that toggle the functions from a classical NP (both renal and vaso-active) to an only vasodilatory peptide.

To understand the role of a C-terminal tail in the in-vivo functions of NPs, the C-terminal tail of K-Ring (RH) was replaced by that of ANP (NSFRY; SEQ ID NO: 57). This variant, K-Ring$^{NSFRY}$, exhibited a ≈15 mmHg drop in MAP for a 2 nmol/kg/min infusion. It showed similar changes in HR and PP (−37.5±15.1 BPM and −7.3±0.7 mmHg; FIGS. 2B, 6A, 6B) as ANP along with diuresis (12.3±3.8 µl/min). The peak of diuresis was delayed by 10 min (FIG. 2C). Thus, chimera K-Ring$^{NSFRY}$ showed predominant characteristics of ANP with delayed renal response. Hence, the presence of NSFRY (SEQ ID NO: 57) tail appears to overcome the presence of D3, R4 and D14 residues within the ring. Thus, the C-terminal tail seems to functions as an alternate, but 'forceful' molecular switch which controls in-vivo pharmacological effects. Thus, through systematic mutation studies, we identified two functional switches for diuresis: two Gly residues within the ring and NSFRY (SEQ ID NO: 57) tail. Using these switches we could manipulate the pharmacological effects of K-ring.

Example 3

Functional Switches are Transferable

To further understand the significance of these switches, we systematically introduced Asp residues (replacing G3 and G14) and Arg residue (replacing G4) in ANP. A 2 nmol/kg/min infusion of $^{DGD}$ANP induced marked increase in urine flow rate (7.9±2.1 µl/min) similar to ANP (8.8±1.3 µl/min), but with much milder changes in MAP, HR and PP (−4.8±2.3 mmHg, −7.8±9 BPM and −4.3±1.4 mmHg, respectively) compared to animals which received 0.2 nmol/kg/min of ANP (−10.1±0.8 mmHg, −47.1±13.5 BPM and −7.7±1.8 mmHg, respectively; FIGS. 3B, 3C, FIGS. 7A, 7B, Table 1). The peak of diuresis with $^{DGD}$ANP was delayed by 10 min, similar to K-Ring$^{NSFRY}$. Thus, this variant has similar activity profile as ANP; diuresis activity precedes hypotension, but the introduction of D3 and D14 has widened the gap between the effective concentrations of the peptide required to induce diuresis and vasodilation. In contrast, infusion of 2 nmol/kg/min of $^{DRD}$ANP displayed potent vascular effects (−18.3±2.3 mmHg in MAP, −66.6±14.6 BPM in HR, −7.9±1.8 mmHg in PP) along with profound renal function (18.7±0.7 µl/min urine flow rate) compared to ANP (FIGS. 3B, 3C, 8A, 8B, Table 1). At a lower dose (0.2 nmol/kg/min), $^{DRD}$ANP manifested similar reduction in BP, HR and PP (−12.9±1.5 mmHg, −37.5±9.5 BPM, −5.8±2.8 mmHg respectively) at an equimolar infusion of ANP, but failed to induce diuresis (Table 1). Thus, $^{DRD}$ANP infusion manifested vasoactivity ahead of renal function (FIGS. 3D, 3E, 8A, 8B). These observations support the role of D3 and D14 residues as functional switches. Residue R4 along with D3 and D14 seems to reverse the in-vivo activities in a dose-dependent manner; hypotension at low doses followed by both vascular and renal activities with subsequent increment in concentration of the peptide (FIGS. 3B, 3C). These results indicate that the functional switches identified in K-Ring are transferable to ANP.

Example 4

Stimulation of Guanylyl Cyclase Activity of NPR-A

Physiologically, ANP interacts with NPR-A and stimulates its guanylyl cyclase activity to elevate the intracellular cGMP levels [Oliver, P. M.; et al., *Proc Natl Acad Sci USA* 94 (26): 14730-5 (1997)]. Previously, we showed that K-Ring is an NPR-A agonist with a 10-fold lower potency compared to ANP [Sridharan, S.; Kini, R. M., *Biochem J* 469 (2): 255-66 (2015)]. To understand the role of various residues in K-Ring and ANP mutants, we evaluated their ability to evoke cGMP response in CHO-K1 cells transiently expressing rat NPR-A receptors (FIGS. 4A, 4B, Table 2). Among the single point mutants of K-Ring, $^{GRD}$K-Ring exhibited 5-fold higher potency, while $^{DRG}$K-Ring and $^{D}$$_{G}$$_{D}$K-Ring exhibited a 3- to 4-fold drop in potency compared to K-Ring. The double mutant $^{GRG}$K-Ring also exhibited 4-fold higher potency compared to K-Ring (FIG. 4A, Table 2). These results indicate that D3G substitution led to an increased potency, while the substitution at other positions led to decreased potency. In the double mutant, substitution of D3 led to increase while the second substitution at D14 led to 20% loss in potency. The introduction of ANP's C-terminal tail in K-Ring$^{NSFRY}$ resulted in 5-fold improved activity. Thus, it is evident that the presence of the first Gly residue at position 3 or the C-terminal tail of ANP improves the efficacy of receptor activation.

ANP mutants $^{DRD}$ANP and $^{DGD}$ANP exhibited 3-fold and 8-fold drop in activity compared to ANP (FIG. 4B, Table 2). Both K-Ring$^{NSFRY}$ and $^{DRD}$ANP elicited equipotent response. The difference in potencies between $^{DRD}$ANP and $^{DRD}$ANP is similar to K-Ring and $^{DGD}$K-Ring, implying that R↔G changes contribute equivalently in both NPs.

We also evaluated the activation kinetics of NPR-A in the presence of the mutant ANP and K-Ring to understand the dynamic changes in cGMP generation which would influence the spatio-temporal distribution of the secondary messenger. A time-chase study of cGMP accumulation at $EC_{50}$ concentrations of the peptides was assessed. ANP evoked an instantaneous increase in cGMP level whereas K-Ring exhibited slower activation kinetics (2 min versus 30 min to produce similar levels of cGMP (FIGS. 4C-4F). The rates of generation of cGMP by single point mutants $^{DRG}$K-Ring, $^{DGD}$K-Ring were slower than K-Ring, whereas $^{GRD}$K-Ring induced a slightly increased rate of cGMP production. The double mutant $^{GRG}$K-Ring exhibited improved activation kinetics (3-fold) compared to K-Ring with the maximum accumulation of cGMP within 10 min. Although $^{GRD}$K-Ring and $^{GRG}$K-Ring had comparable $EC_{50}$ concentrations the activation kinetics was distinctly different (the peak of cGMP production was 10 min and 20 min respectively). K-Ring$^{NSFRY}$ showed similar improvement in activation kinetics as $^{GRG}$K-Ring; with a peak response at 10 min followed by a slow decay of cGMP to reach the saturation value. The variants of ANP showed slower activation kinetics compared to the wild type; both $^{DRD}$ANP and $^{DGD}$ANP showed 2.6- and 7.8-times slower kinetics (maximum cGMP elevation at 10 min). $^{DGD}$ANP exhibits faster decay of intracellular cGMP compared to $^{DRD}$ANP. These observations suggest that D residues indeed influence receptor binding and secondary messenger generation. The variants which exhibited faster activation kinetics seemed to show a decay of cGMP after the peak response. Since the cells were treated with phosphodiesterase inhibitor (0.5 mM IBMX), most likely the rate of degradation of cGMP was negligible. The treatment of the cells with $EC_{50}$ concentration of the peptide ensured the cellular GTP was not limiting. Hence, the observed decay in cGMP production in certain variants suggests that these peptides most likely caused desensitization of the receptor.

Overall, the activation kinetics of NPR-A clearly distinguishes various NP mutants; vasoactive NPs exhibit slower kinetics compared vaso- and renal active NPs exhibit relatively faster kinetics.

TABLE 1

Summary of in-vivo responses of ANP, K-Ring and their variants

| Peptide (nmol/kg/min) | Mean arterial pressure | | | Heart rate | | | Pulse pressure | | | Urine flow rate | | |
|---|---|---|---|---|---|---|---|---|---|---|---|---|
| | Peak response (mmHg) | Peak time (min) | Recovery | Peak response (BPM) | Peak time (min) | Recovery | Peak response (mmHg) | Peak time (min) | Recovery | Peak response (µl/min) | Peak Time (min) | Recovery |
| ANP (0.08) | −1.6 ± 1.5 | — | — | −7.8 ± 2.4 | — | — | −2.1 ± 1.5 | — | — | 5.4 ± 1.4 | 20 | Y |
| ANP (0.2) | −10.1 ± 1.9 | 30 | Y | −47.1 ± 13.5 | 30 | Y | −7.7 ± 3.9 | 40 | Y | 8.8 ± 1.3 | 20 | Y |
| K-Ring (2.0) | −11.8 ± 2.4 | 30 | Y | −22.2 ± 12.1 | 20 | Y | −4.5 ± 1.7 | 20 | — | <2 | — | — |
| K-Ring (10.0) | −17.9 ± 2.2 | 30 | N | −24.9 ± 4.3 | 30 | Y | −5.6 ± 2.6 | 30 | Y | <2 | — | — |
| $^{GRD}$K-Ring (2.0) | −11.3 ± 4.3 | 30 | Y | −44.8 ± 20.1 | 30 | Y | −11.4 ± 2.4 | 20 | Y | <2 | — | — |
| $^{DRG}$K-Ring (2.0) | −10.5 ± 1.2 | 30 | N | −18.8 ± 3.2 | 40 | N | −3.2 ± 3.0 | — | — | <2 | — | — |
| $^{DGD}$K-Ring (2.0) | −12.5 ± 2 | 30 | Y | −21.9 ± 9.8 | 30 | Y | −5.8 ± 0.9 | 30 | Y | <2 | — | — |
| $^{GRG}$K-Ring (2.0) | −11.6 ± 1.5 | 30 | Y | −39.0 ± 2.8 | 20 | Y | −12.9 ± 0.8 | 30 | Y | 11.4 ± 3.8 | 20 | Y |
| K-Ring$^{NSFRY}$ (2.0) | −15.1 ± 1.4 | 30 | Y | −37.4 ± 15.4 | 30 | Y | −7.3 ± 0.7 | 30 | Y | 10.8 ± 2.9 | 30 | Y |
| $^{DGD}$ANP (2.0) | −4.8 ± 2.9 | — | — | −7.5 ± 8.9 | — | — | −4.5 ± 1.4 | — | — | 7.9 ± 2.0 | 30 | Y |
| $^{DRD}$AND (2.0) | −18.4 ± 2.4 | 30 | Y | −66.6 ± 14.5 | 30 | N | −8.0 ± 1.8 | 20 | Y | 18.8 ± 0.7 | 20 | Y |
| $^{DRD}$ANP (0.2) | −12.9 ± 1.5 | 30 | Y | −37.5 ± 9.5 | 30 | Y | −5.9 ± 2.0 | 20 | Y | <2 | — | — |

Experiments consisted of six 10 min points. One control period (0-10 min), one infusion period (10-20 min), four recovery periods (10-30 min, 30-40 min, 40-50 min and 50-60 min). The end represented is the average responses over the 10 min period from five independent trials.

TABLE 2

Summary of receptor activation potency and kinetics of ANP, K-Ring and their variants

| Peptide | NPR-A activation potency IC$_{50}$ (nM) | Ratio compared ANP | Ratio compared wild type NPs | Rate of generation of cGMP (pmol cGMP/pmol peptide) | Ratio compared ANP | Ratio compared wild type NPs |
|---|---|---|---|---|---|---|
| ANP | 17.3 | 1 | 1 | 7.97 | 1 | 1 |
| K-Ring | 243.7 | 14.1 | 1 | 0.0228 | 349.6 | 1 |
| $^{GRD}$K-Ring | 50.7 | 2.9 | −4.8 | 0.113 | 70.5 | 5.0 |
| $^{DRG}$K-Ring | 693.8 | 40.1 | 2.8 | 0.007 | 1138.6 | 3.2 |
| $^{DGD}$K-Ring | 866.2 | 50.1 | 3.6 | 0.005 | 1594.0 | 4.6 |
| $^{GRG}$K-Ring | 87.7 | 5.1 | −2.8 | 0.19 | 41.9 | 8.3 |
| K-Ring$^{NSFRY}$ | 43.8 | 2.5 | −5.6 | 0.31 | 25.7 | 13.6 |
| $^{DGD}$ANP | 134.9 | 7.8 | 7.8 | 0.14 | 56.9 | 56.9 |
| $^{DRD}$ANP | 45.2 | 2.6 | 2.6 | 0.38 | 21.0 | 21.0 |

TABLE 3

Masses of ANP, K-Ring and their variants

| Peptide | Calculated oxidized mass (Da) | Observed mass (Da) |
|---|---|---|
| K-Ring | 2769.1 | 2768.9 ± 0.4 |
| $^{DRG}$K-Ring | 2711.1 | 2711.6 ± 0.3 |
| $^{GRD}$K-Ring | 2711.1 | 2711.1 ± 0.4 |
| $^{DGD}$K-Ring | 2670.2 | 2670.2 ± 0.3 |
| $^{GRG}$K-Ring | 2653.0 | 2653.3 ± 0.2 |
| K-Ring$^{NSFRY}$ | 3143.1 | 3143.2 ± 0.2 |
| ANP | 3080.4 | 3080.5 ± 0.5 |
| $^{DGD}$ANP | 3196.2 | 3196.6 ± 0.3 |
| $^{DRD}$ANP | 3277.6 | 3277.8 ± 0.2 |

TABLE 4

Rate of change of HR and PP per unit change in MAP of ANP, K-Ring and variants

| Peptide | HR | | PP | |
|---|---|---|---|---|
| | Rate of change | Correlation efficient | Rate of change | Correlation efficient |
| K-Ring | 1.7 | 0.66 | 0.5 | 0.67 |
| $^{DRG}$K-Ring | 1.6 | 0.89 | 0.25 | 0.44 |
| $^{GRD}$K-Ring | 2.82 | 0.93 | 0.7 | 0.8 |
| $^{DGD}$K-Ring | 1.5 | 0.78 | 0.4 | 0.75 |
| $^{GRG}$K-Ring | 3.1 | 0.80 | 1.2 | 0.9 |
| K-Ring$^{NSFRY}$ | 2.4 | 0.92 | 0.42 | 0.75 |
| ANP* | 5.6 | 0.95 | 0.5 | 0.65 |
| $^{DGD}$ANP | 4.4 | 0.44 | 0.5 | 0.4 |
| $^{DRD}$ANP | 4.5 | 0.95 | 0.5 | 0.6 |

The data represented in the correlation between MAP and other vascular parameter for an infusion of 2 nmol/kg/min of peptide except ANP (0.2 nmol/kg/min)

Discussion

The antihypertensive and anti-hypervolemic properties of ANP are concentration-dependent; exclusive renal functions manifest at a lower dose (0.02-0.1 nmol/kg/min) and both the activities are exhibited at slightly higher doses (>0.1 nmol/kg/min) [Morice, A.; et al., Clin Sci (Lond) 74 (4): 359-63 (1988)]. Thus, the differences in the threshold concentrations that segregate the activity on kidney and circulation are less than 5-fold apart and are variable among different studies [Soejima, H.; et al., Am J Physiol 255 (3 Pt 2): R449-55 (1988); Morice, A.; et al., Clin Sci (Lond) 74 (4): 359-63 (1988)]. Although this dose dependency may be attributed to the NPR-A expression levels in the target tissues (kidney>blood vessels) [Uhlen, M.; et al., Science 347 (6220): 1260419 (2015)], the exact molecular mechanisms are unclear. Structure-activity studies of ANP have identified vital residues (F8, M13, D14, and R15 within the ring and the C-terminal NSFRY; SEQ ID NO: 57) which are necessary for NPR-A binding [Olins, G. M.; et al., J Biol Chem 263 (22): 10989-93 (1988)] and conferring the physiological activity. Several studies have utilized phage display to increase the specificity of ANP variants to NPR-A and improve the natriuretic/diuretic response [Jin, H.; Li, B.; et al., J Clin Invest 98 (4): 969-76 (1996)]. However, the molecular determinants of vascular and renal function in NPs remain unidentified.

Recently we identified and characterized an exogenous NP from krait venom (KNP) [Sridharan, S.; Kini, R. M., Biochem J 469 (2): 255-66 (2015)]. This peptide has the conserved NP ring with a 38-residue long C-terminal tail (FIG. 1A) which had propensity to form α-helix. Our structure-function studies showed that KNP has two pharmacophores: K-Ring and Helix. These functional segments induced vasodilation through orthogonal pathways. K-Ring, like a classical NP, elevates intracellular cGMP levels through activation of NPR-A with a 10-fold lower potency compared to ANP, while Helix uses NO-dependent mechanisms [Sridharan, S.; Kini, R. M., Biochem J 469 (2): 255-66 (2015)].

Figures 1A, 1B, 1C:
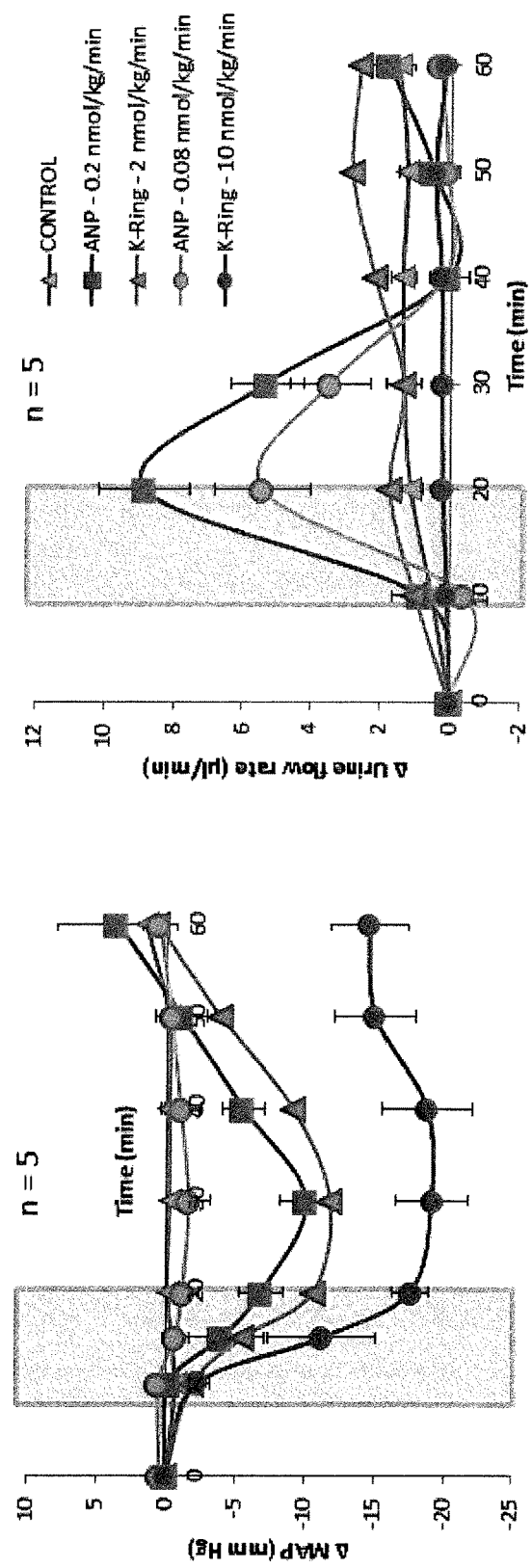
FIGS. 1A-1C show K-Ring is a vasodilator.

Further, we observed that the infusion of 2 nmol/kg/min of K-Ring in anesthetized rats showed a 12 mmHg drop in mean arterial pressure (MAP) (recovered to baseline within experimental period) without significant changes in urine volume [Sridharan, S.; Kini, R. M., Biochem J 469 (2): 255-66 (2015)]. A 5-times higher dose of K-Ring showed further drop in MAP (−19.1±2.5 mmHg with no recovery) without affecting urine volume (FIGS. 1B, 1C). Thus, K-ring induced vasodilation with minimal or no diuretic effects. This is in contrast to ANP's ability to induce diuretic and vasodilatory activities; ANP at a low dose (0.08 nmol/kg/min) showed increased urine volume without any alteration in MAP while a slightly higher dose (0.2 nmol/kg/min) showed both reduction in MAP along with diuresis (FIGS. 1B, 1C), as was observed previously [Soejima, H.; et al., Am J Physiol 255 (3 Pt 2): R449-55 (1988)]. Thus the observed difference in the in-vivo activity of these peptides suggested that, K-Ring has distinct hemodynamic and diuretic effects compared to ANP and it could serve as a molecular roadmap to delineate the determinants of hypotensive and diuretic functions in NPs.

Structure-activity studies on ANP have shown that certain conserved residues (F2, M6, D7, R8, 19 and L15) within the 17-membered ring and its C-terminal tail (NSFRY; SEQ ID NO: 57) are crucial for NPR-A binding and in-vivo activity [Li, B.; et al., Science 270 (5242): 1657-60 (1995); Olins, G. M.; et al., J Biol Chem 263 (22): 10989-93 (1988); Ogawa, H.; et al., J Biol Chem 279 (27): 28625-31 (2004)]. All critical residues necessary for receptor binding within the ring are conserved in K-Ring, but its C-terminal tail has only two residues (RH). In comparison to ANP, K-Ring has several substitutions within the ring (G3D, G4R, G9S, A10T, Q11H and G14D). Among these, residues at positions 9, 10 and 11 are variable among several NPs (FIG. 1A). Thus, we hypothesized that the distinct structural differences, G3D, G4R and G14D substitutions along with shorter C-terminal tail, may be responsible for the observed differences in the hemodynamic and diuretic effects of ANP and K-Ring. In the present study, we address their role in imparting the in-vivo functions of NPs using systematic substitution. Further, using deciphered structural details we have engineered ANP analogues with either vascular or renal functions. Such variants with exclusive functions have immense value as therapeutic agents in treating heart failure patients. These structure-function relationship studies also identify the key residues that impact on NP-induced vasodilation, heart rate and diuresis.

K-Ring Helps in Delineation of Vasodilatory and Diuretic Effects

Our previous study showed that K-Ring (70% identical to ANP) exclusively induced hypotensive effects without altering renal output, despite being an NPR-A agonist [Sridharan, S.; Kini, R. M., Biochem J 469 (2): 255-66 (2015)]. This peptide failed to evoke renal response even at 100-fold higher concentrations than ANP that induced exclusive diuresis (FIGS. 1B, 1C). Hence, K-Ring structure seemed to encode the molecular information that governs tissue-specific responses of NPs and thus, provided impetus to identify the residues, which play critical role in determining selectivity towards vascular and/or renal functions and act as functional switches.

Role of G3: G3 is conserved in almost all NPs. But this residue is replaced by Asp in K-ring (FIG. 1A). Our results suggest that G3 is a crucial residue within the ring of NP which imparts potent vascular functions. The substitution of this residue with negatively charged Asp decreased the potency to activate NPR-A by ~3- to 10-fold (FIG. 4A, B, Table 2) and lowered the activation kinetics (5-fold) (FIG. 4C, D, Table 2). G3D substitution also seemed to lower the influence on HR and PP, for similar BP changes (FIG. 2A, 6A, B); D3 variants showed smaller change in HR and PP per mm Hg drop in BP (1.5 times and 0.3 times, respectively) compared to G3 variants (3.0 times and 0.8 times, respectively) (Table 4). Thus, G3↔D3 changes acted as the molecular switches which controlled the HR and PP changes of a NP.

Role of G14: Within K-Ring scaffold, the substitution of D14 to G appeared to lower the potency of NPR-A by 10-fold (Table 2) and activation kinetics by 3-fold (FIG. 4C). This variation at positon 14 seemed to sustain the change in BP and HR all throughout the experimental period with minimal recovery. Hence, it may be suggested that G14 is key residue necessary to elicit sustained vascular activity. In comparison between $^{GRG}$K-Ring, $^{DRG}$K-Ring and $^{GRD}$K-Ring, it is evident that G14 controlled the renal function of a NP. The presence of both G3 and G14 are necessary to warrant renal functions to NPs.

The residues D3 and D14 seem to lower ability of a NP to evoke cGMP response. From the crystal structure of ANP-NPR-A complex, G3 and G14 seem to be in close proximity with a negatively charged pocket (E169A and E169B of receptor subunits) [Ogawa, H.; et al., J Biol Chem 279 (27): 28625-31 (2004)]. The presence of D in the place G could introduce conformational constraint as well as electrostatic repulsion between the negatively charged pocket of NPR-A, which might disengage key molecular interactions and mediate activation through a varied set of structural framework compared to high affinity native ligands. The differences in the conformational selectivity imposed on the extracellular domain by different ligands may alter the relay of allosteric activation of intracellular guanylcyclase domain thereby leading to distinctive activation kinetics. Previous studies have shown that the mutations of G3A and G14A did not alter the binding efficiency significantly, suggesting that the loss of conformational flexibility in the absence of Gly residues had no influence [Li, B.; et al., *Science* 270 (5242): 1657-60 (1995); Watanabe, T. X.; et al., *Eur J Pharmacol* 147 (1): 49-57 (1988)]. Thus, our results indicate that the incorporation of Asp residues at 3 and 14 and introduction of bulkier and charged side chain might lower the ligand's ability to activate NPR-A and influence its in-vivo activity.

Role of G4: Substitution of G4 to Arg seemed to improve the NPR-A activation potency by 3-fold. The difference in activity was observed between $^{DGD}$K-Ring and K-Ring as well as $^{\underline{DGD}}$ANP and $^{\underline{DRD}}$ANP suggesting that R4 may be important to compensate the disengagement of interaction with NPR-A due to the introduction of negatively charged residues in both the scaffolds. This residue seems to be important for reversal of function selectivity (vasoactivity followed by renal) in ANP frame work. $^{DGD}$K-Ring induces a slower rate of BP decrease compared to $^{DRD}$K-Ring, suggesting the lower influence on the system (FIGS. 2B, 2C). The NP variants with G3 and G14 exhibited 10-fold improved NPR-A activation potency and 3-fold faster kinetics compared to the variants with Asp in these positions. Both G3 and G14 seemed to be the necessary to display renal activity in K-Ring scaffold and hence identified as 'diuretic switch residues'.

Role of the C-terminal NSFRY (SEQ ID NO: 57): The C-terminal NSFRY (SEQ ID NO: 57) acts as the alternate, but 'forceful' diuretic functional switch which introduces renal function in peptides which are exclusively hypotensive. Addition of C-terminal tail to K-Ring improves NPR-A activation potency (5-fold) and kinetics (10-fold). The crystal structure of ANP-NPR-A shows residues N, S, F, R of the C-terminal tail form hydrogen bonding and pi-pi interaction with Q186B, E187B and F188B of the receptor. Earlier mutagenesis studies also revealed that the absence of the C-terminal tail decreases the ability to elicit vasorelaxation (30-fold) and natriuresis (3-fold) of ANP [Watanabe, T. X.; et al., *Eur J Pharmacol* 147 (1): 49-57 (1988)]. Thus C-terminal tail appears to be an important molecular switch. The presence of the C-terminal tail increases the influence on HR and PP (FIGS. 3A-3C, 7A-7D). Thus, the addition of C-terminal tail improved the vascular activity and imparted renal functions. Although both $^{\underline{DRD}}$ANP and K-Ring$^{\underline{NSFRY}}$ elicited equipotent activation potency and kinetics of NPR-A, equimolar infusion of these peptides resulted in $^{\underline{DRD}}$ANP exhibiting influence on HR (2-fold) and diuresis (2-fold) compared to K-Ring$^{\underline{NSFRY}}$ (Table 1).

The inclusion of NSFRY (SEQ ID NO: 57) as C-terminal tail in K-Ring scaffold showed a delayed diuresis peak compared to $^{\underline{DRD}}$ANP (FIG. 3C). These differences in the in-vivo effects may be attributed to the structural differences in positions 9, 10 and 11 (G, A, Q in ANP versus S, H, T in K-Ring) between the two NPs. A previous study using phage display library showed that G9R, A10E and Q11A mutations seemed to improve natriuretic and diuretic functions [Cunningham, B. C.; et al., *EMBO J* 13 (11): 2508-15 (1994)]. Thus, further studies are needed to evaluate the roles of these residues in the renal functions of an NP.

NPR-A Receptor Activation Kinetics and Function

The differences in the pharmacological functions of NP variants may be explained through: (a) expression level of NPR-A in different target tissues; (b) expression pattern of clearance receptor (NPR-C); (c) binding and activation kinetics of the ligand; and (d) compartmentalization of signals. Gene expression levels and histochemical staining experiments reveal higher levels of NPR-A expression in kidney compared to vascular smooth muscle [Uhlen, M.; et al., *Science* 347 (6220): 1260419 (2015)]. Although NPR-C expression follows a similar trend (expression higher in kidney compared to vascular smooth muscle) the ratios of NPR-A and NPR-C in these tissues, which determines the activation profile, are different [Uhlen, M.; et al., *Science* 347 (6220): 1260419 (2015)]. The onset of renal functions at low doses of ANP may be attributed to the differential in the expression pattern of receptors in the target tissue. All NP analogues activated NPR-A but their activation kinetics varied significantly (Table 2). The data show that (i) exclusively hypotensive peptides exhibited slow activation kinetics compared to both diuretic and vasodilatory peptides and (ii) peptides exhibiting faster activation showed decay of cGMP signal after a peak response. This difference in the rate of synthesis of cGMP would alter the diffusion rates, which might introduce differential spatio-temporal distribution and compartmentalization of the signal to activate only certain downstream effectors leading to selective downstream function [Piggott, L. A.; et al., *J Gen Physiol* 128 (1): 3-14 (2006)]. The key downstream effectors in both cell types are protein kinase G (cytosolic), phosphodiesterase (both cytosolic and membrane associated) and cyclic nucleotide gated ion channels (membrane bound) [Potter, L. R.; et al., *Handb Exp Pharmacol* (191): 341-66 (2009)]. The differential localization of these proteins necessitates the diffusion of the secondary messenger to initiate the signaling cascade. There is substantial evidence enunciating the role of phosphodiesterases in compartmentalizing cyclic nucleotide signals [Fischmeister, R.; et al., *Circ Res* 99 (8): 816-28 (2006)] and this 2006 study suggests that diffusion enhanced spatial segregation of signal contours may aid in attributing specific downstream functions. Thus, further characterization of the differences in intracellular signals imposed by the native ligands (ANP and BNP) or NP analogues described here may help us understand how these peptides exhibit distinct physiological or pharmacological profiles.

Delinking Vasodilatory and Diuretic Functions of NPs

Our study delineated the salient features of NPs and identified the molecular functional switches that determine vasodilatory and/or diuretic functions of NPs. Asp residues at position 3 and 14 in the absence of the C-terminal tail are the key salient feature to develop only vasoactive NPs. Residue G3 seems to cause greater drop in HR and PP, and its substitution with Asp lowers the reduction of these parameters for a similar change in MAP. The presence of G3 and G14 or the presence of the C-terminal tail leads to diuretic functions. As mentioned above, HF scenarios need personalized medicine depending on pressure-volume overload. These functional switches help create NPs which are adjustable to the personalized treatments of HF patients. Thus, this study presents the design of potential NP analogues which could help in the development key therapeutic molecules. The present study investigates the pharmacological roles of these peptides in anesthetized rats.

In conclusion, this study has pinpointed the molecular switches which control the activity of NPs on smooth muscle and kidney. This study widens the scope for design of ligands for specific needs and provides a platform to explore the receptor-effector system of NPR-A. The engineered NP analogues may serve as key therapeutic leads that could help regulate either blood pressure or volume in distinct cohorts of HF patients.

Summary

Natriuretic peptides have crucial effects in restoring the equilibrium during heart failure. ANP elicits a concentration-dependent diuretic and/or hypotensive functions; at low doses it elicits only renal function and at slightly higher doses it elicits both vascular and renal functions. K-Ring, the conserved ring of krait venom NP, exhibited exclusive vasodilatory effects without altering urine volume at 100-times the concentration of ANP. Here, we have delineated the molecular switches that control its vasodilatory and diuretic functions through systematic substitution of residues at positions 3, 4 and 14 within the ring and C-terminal tail. Infusion of various NP analogues in anesthetized rats indicated that (a) G3 analogues significantly reduced the heart rate and pulse pressure compared to D3 analogues;
(b) G4 analogues exhibited exclusive diuresis at low dose and hypotension along with diuresis at higher dose while R4 analogues elicited a reversed preference of pharmacological activity;
(c) G14 analogues showed sustained vasodilatory effects compared to D14 analogues;

(d) analogues with both G3 and G14 substitutions elicited diuresis, while D3 and D14 analogues exhibited exclusive hypotension without significant diuresis, thereby acting as 'vasodilatory-diuresis toggle' switch; and (e) the analogue with the C-terminal tail (NSFRY; SEQ ID NO: 57) overrides the influence of D3 and D14 residues to induce diuresis in otherwise only vasodilatory peptides, thereby acting as 'forceful diuresis' switch. NPR-A activation potencies and kinetics of these peptides distinguish the observed pharmacological profile; partial agonists with slow activation kinetics exhibited only vasodilatory properties, while those with faster kinetics elicited both vasodilatory and diuretic effects.

REFERENCES

Any listing or discussion of an apparently prior-published document in this specification should not necessarily be taken as an acknowledgement that such document is part of the state of the art or is common general knowledge.

Brenner, B. M.; Ballermann, B. J.; Gunning, M. E.; Zeidel, M. L., Diverse biological actions of atrial natriuretic peptide. *Physiol Rev* 1990, 70 (3), 665-99.

Chusho, H.; Tamura, N.; Ogawa, Y.; Yasoda, A.; Suda, M.; Miyazawa, T.; Nakamura, K.; Nakao, K.; Kurihara, T.; Komatsu, Y.; Itoh, H.; Tanaka, K.; Saito, Y.; Katsuki, M.; Nakao, K., Dwarfism and early death in mice lacking C-type natriuretic peptide. *Proc Natl Acad Sci USA* 2001, 98 (7), 4016-21.

Cunningham, B. C.; Lowe, D. G.; Li, B.; Bennett, B. D.; Wells, J. A., Production of an atrial natriuretic peptide variant that is specific for type A receptor. *EMBO J* 1994, 13 (11), 2508-15.

de Bold, A. J., Atrial natriuretic factor: a hormone produced by the heart. *Science* 1985, 230 (4727), 767-70.

Fischmeister, R.; Castro, L. R.; Abi-Gerges, A.; Rochais, F.; Jurevicius, J.; Leroy, J.; Vandecasteele, G., Compartmentation of cyclic nucleotide signaling in the heart: the role of cyclic nucleotide phosphodiesterases. *Circ Res* 2006, 99 (8), 816-28.

Jin, H.; Li, B.; Cunningham, B.; Tom, J.; Yang, R.; Sehl, P.; Thomas, G. R.; Ko, A.; Oare, D.; Lowe, D. G., Novel analog of atrial natriuretic peptide selective for receptor-A produces increased diuresis and natriuresis in rats. *J Clin Invest* 1996, 98 (4), 969-76.

Kangawa, K.; Matsuo, H., Purification and complete amino acid sequence of alpha-human atrial natriuretic polypeptide (alpha-hANP). *Biochem Biophys Res Commun* 1984, 118 (1), 131-9;

Lee, C. Y.; Burnett, J. C., Jr., Natriuretic peptides and therapeutic applications. *Heart Fail Rev* 2007, 12 (2), 131-42.

Li, B.; Tom, J. Y.; Oare, D.; Yen, R.; Fairbrother, W. J.; Wells, J. A.; Cunningham, B. C., Minimization of a polypeptide hormone. *Science* 1995, 270 (5242), 1657-60;

Maack, T.; Atlas, S. A.; Camargo, M. J.; Cogan, M. G., Renal hemodynamic and natriuretic effects of atrial natriuretic factor. *Fed Proc* 1986, 45 (7), 2128-32; (b) Sasaki, A.; Kida, O.; Kangawa, K.; Matsuo, H.; Tanaka, K., Hemodynamic effects of alpha-human atrial natriuretic polypeptide (alpha-hANP) in rats. *Eur J Pharmacol* 1985, 109 (3), 405-7.

MacMahon, K. M.; Lip, G. Y., Psychological factors in heart failure: a review of the literature. *Arch Intern Med* 2002, 162 (5), 509-16.

McMurray, J. J.; Pfeffer, M. A., Heart failure. *Lancet* 2005, 365 (9474), 1877-89.

Morice, A.; Pepke-Zaba, J.; Loysen, E.; Lapworth, R.; Ashby, M.; Higenbottam, T.; Brown, M., Low dose infusion of atrial natriuretic peptide causes salt and water excretion in normal man. *Clin Sci* (*Lond*) 1988, 74 (4), 359-63.

Mukaddam-Daher, S., Natriuretic peptides as therapeutic targets. *Expert Opin Ther Targets* 2006, 10 (2), 239-52.

Ogawa, H.; Qiu, Y.; Ogata, C. M.; Misono, K. S., Crystal structure of hormone-bound atrial natriuretic peptide receptor extracellular domain: rotation mechanism for transmembrane signal transduction. *J Biol Chem* 2004, 279 (27), 28625-31.

Olins, G. M.; Patton, D. R.; Bovy, P. R.; Mehta, P. P., A linear analog of atrial natriuretic peptide (ANP) discriminates guanylate cyclase-coupled ANP receptors from non-coupled receptors. *J Biol Chem* 1988, 263 (22), 10989-93;

Oliver, P. M.; Fox, J. E.; Kim, R.; Rockman, H. A.; Kim, H. S.; Reddick, R. L.; Pandey, K. N.; Milgram, S. L.; Smithies, O.; Maeda, N., Hypertension, cardiac hypertrophy, and sudden death in mice lacking natriuretic peptide receptor A. *Proc Natl Acad Sci USA* 1997, 94 (26), 14730-5.

Packer, M., How should physicians view heart failure? The philosophical and physiological evolution of three conceptual models of the disease. *Am J Cardiol* 1993, 71 (9), 3C-11C, Piggott, L. A.; Hassell, K. A.; Berkova, Z.; Morris, A. P.; Silberbach, M.; Rich, T. C., Natriuretic peptides and nitric oxide stimulate cGMP synthesis in different cellular compartments. *J Gen Physiol* 2006, 128 (1), 3-14.

Potter, L. R.; Yoder, A. R.; Flora, D. R.; Antos, L. K.; Dickey, D. M., Natriuretic peptides: their structures, receptors, physiologic functions and therapeutic applications. *Handb Exp Pharmacol* 2009, (191), 341-66.

Roger, V. L.; Go, A. S.; Lloyd-Jones, D. M.; Adams, R. J.; Berry, J. D.; Brown, T. M.; et al.; American Heart Association Statistics, C.; Stroke Statistics, S., Heart disease and stroke statistics—2011 update: a report from the American Heart Association. *Circulation* 2011, 123 (4), e18-e209.

Rogers, C.; Bush, N., Heart Failure: Pathophysiology, Diagnosis, Medical Treatment Guidelines, and Nursing Management. *Nurs Clin North Am* 2015, 50 (4), 787-99.

Soejima, H.; Grekin, R. J.; Briggs, J. P.; Schnermann, J., Renal response of anesthetized rats to low-dose infusion of atrial natriuretic peptide. *Am J Physiol* 1988, 255 (3 Pt 2), R449-55.

Sridharan, S.; Kini, R. M., Tail wags the dog: activity of krait natriuretic peptide is determined by its C-terminal tail in a natriuretic peptide receptor-independent manner. *Biochem J* 2015, 469 (2), 255-66.

Strobeck, J. E.; Silver, M. A., Beyond the four quadrants: the critical and emerging role of impedance cardiography in heart failure. *Congest Heart Fail* 2004, 10 (2 Suppl 2), 1-6.

Sudoh, T.; Kangawa, K.; Minamino, N.; Matsuo, H., A new natriuretic peptide in porcine brain. *Nature* 1988, 332 (6159), 78-81;

Sudoh, T.; Minamino, N.; Kangawa, K.; Matsuo, H., C-type natriuretic peptide (CNP): a new member of natriuretic peptide family identified in porcine brain. *Biochem Biophys Res Commun* 1990, 168 (2), 863-70.

Suga, S.; Nakao, K.; Hosoda, K.; Mukoyama, M.; Ogawa, Y.; Shirakami, G.; Arai, H.; Saito, Y.; Kambayashi, Y.; Inouye, K.; et al., Receptor selectivity of natriuretic peptide family, atrial natriuretic peptide, brain natriuretic peptide, and C-type natriuretic peptide. *Endocrinology* 1992, 130 (1), 229-39.

Suga, S.; Itoh, H.; Komatsu, Y.; Ogawa, Y.; Hama, N.; Yoshimasa, T.; Nakao, K., Cytokine-induced C-type natriuretic peptide (CNP) secretion from vascular endothelial cells—evidence for CNP as a novel autocrine/paracrine regulator from endothelial cells. *Endocrinology* 1993, 133 (6), 3038-41.

Uhlen, M.; Fagerberg, L.; Hallstrom, B. M.; Lindskog, C.; Oksvold, P.; Mardinoglu, A.; et al., Proteomics. Tissue-based map of the human proteome. *Science* 2015, 347 (6220), 1260419.

Volpe, M.; Carnovali, M.; Mastromarino, V., The natriuretic peptides system in the pathophysiology of heart failure: from molecular basis to treatment. *Clin Sci (Lond)* 2016, 130 (2), 57-77.

Waldman, S. A.; Rapoport, R. M.; Murad, F., Atrial natriuretic factor selectively activates particulate guanylate cyclase and elevates cyclic GMP in rat tissues. *J Biol Chem* 1984, 259 (23), 14332-4.

Watanabe, T. X.; Noda, Y.; Chino, N.; Nishiuchi, Y.; Kimura, T.; Sakakibara, S.; Imai, M., Structure-activity relationships of alpha-human atrial natriuretic peptide. *Eur J Pharmacol* 1988, 147 (1), 49-57.

The invention claimed is:

1. An isolated peptide having vasodilatory and/or diuretic activity in mammals, wherein the isolated peptide is selected from the group consisting of:

```
                                                (SEQ ID NO: 46)
SLRRSSCFGRRMDRIGAQSGLGCNSFRY;

(SEQ ID NO: 47)
SLRRSSCFGGRMDRIGAQSDLGCNSFRY;

(SEQ ID NO: 48)
SLRRSSCFDRRMDRIGAQSGLGCNSFRY;

(SEQ ID NO: 49)
SLRRSSCFDGRMDRIGAQSDLGCNSFRY;

(SEQ ID NO: 50)
SLRRSSCFGRRMDRIGAQSDLGCNSFRY;
and (SEQ ID NO: 51)
SLRRSSCFDRRMDRIGAQSDLGCNSFRY.
```

2. An isolated peptide of claim 1, wherein the isolated peptide is SLRRSSCFDRRMDRIGAQSDLGCNSFRY (SEQ ID NO: 51) and has vasodilatory activity; or the isolated peptide is SLRRSSCFDGRMDRIGAQSDLGCNSFRY (SEQ ID NO: 49) and has renal activity.

3. An isolated peptide of claim 1 in admixture with a pharmaceutically acceptable adjuvant, diluent, or carrier.

4. A composition comprising the isolated peptide of claim 1.

5. The isolated peptide of claim 1, wherein the isolated peptide comprises the sequence set forth in SLRRSSCFDRRMDRIGAQSDLGCNSFRY (SEQ ID NO: 51).

6. The isolated peptide of claim 1, wherein the isolated peptide comprises the sequence set forth in SLRRSSCFGRRMDRIGAQSGLGCNSFRY (SEQ ID NO: 46).

7. The isolated peptide of claim 1, wherein the isolated peptide comprises the sequence set forth in SLRRSSCFGGRMDRIGAQSDLGCNSFRY (SEQ ID NO: 47).

8. The isolated peptide of claim 1, wherein the isolated peptide comprises the sequence set forth in SLRRSSCFDRRMDRIGAQSGLGCNSFRY (SEQ ID NO: 48).

9. The isolated peptide of claim 1, wherein the isolated peptide comprises the sequence set forth in SLRRSSCFDGRMDRIGAQSDLGCNSFRY (SEQ ID NO: 49).

10. The isolated peptide of claim 1, wherein the isolated peptide comprises the sequence set forth in SLRRSSCFGRRMDRIGAQSDLGCNSFRY (SEQ ID NO: 50).

11. An isolated peptide having vasodilatory and/or diuretic activity in mammals, comprising:

a) the amino acid sequence $CFX_1X_2X_3X_4DRIX_5X_6X_7SX_8X_9GCNSFRY$ (SEQ ID NO: 23), wherein $X_1$ is D; $X_2$ is G or R; $X_3$ is R or K; $X_4$ is M; $X_5$ is G, S, or N; $X_6$ is A, H, or S; $X_7$ is Q, T, S, M, or V; $X_8$ is G or D; and $X_9$ is I or L; or b) the amino acid sequence SLRRSSCFDGRMERIGAQSGLGCNSFRY (SEQ ID NO: 45).

12. An isolated peptide having vasodilatory and/or diuretic activity in mammals, comprising:

a) the amino acid sequence $CFX_1X_2X_3X_4DRIX_5X_6X_7SX_8X_9GCNSFRY$ (SEQ ID NO: 23), wherein $X_1$ is G or D; $X_2$ is G or R; $X_3$ is R or K; $X_4$ is M; $X_5$ is G, S, or N; $X_6$ is A, H, or S; $X_7$ is Q, T, S, M, or V; $X_8$ is D; and $X_9$ is I or L; or b) the amino acid sequence SLRRSSCFDGRMERIGAQSGLGCNSFRY (SEQ ID NO: 45).

* * * * *

SEQUENCE LISTING

```
<160> NUMBER OF SEQ ID NOS: 57

<210> SEQ ID NO 1
<211> LENGTH: 17
<212> TYPE: PRT
<213> ORGANISM: Artificial Sequence
<220> FEATURE:
<223> OTHER INFORMATION: K-ring derived 17 aa peptide #1
<220> FEATURE:
<221> NAME/KEY: MISC_FEATURE
<222> LOCATION: (3)..(4)
<223> OTHER INFORMATION: Xaa comprises any amino acid
<220> FEATURE:
<221> NAME/KEY: MISC_FEATURE
<222> LOCATION: (5)..(5)
<223> OTHER INFORMATION: Xaa comprises R or K
<220> FEATURE:
<221> NAME/KEY: MISC_FEATURE
<222> LOCATION: (6)..(6)
<223> OTHER INFORMATION: Xaa comprises M, I or L
<220> FEATURE:
<221> NAME/KEY: MISC_FEATURE
<222> LOCATION: (10)..(10)
<223> OTHER INFORMATION: Xaa comprises G, S or N
<220> FEATURE:
<221> NAME/KEY: MISC_FEATURE
<222> LOCATION: (11)..(11)
<223> OTHER INFORMATION: Xaa comprises A, H or S
<220> FEATURE:
<221> NAME/KEY: MISC_FEATURE
<222> LOCATION: (12)..(12)
<223> OTHER INFORMATION: Xaa comprises Q, T, S, M or V
<220> FEATURE:
<221> NAME/KEY: MISC_FEATURE
<222> LOCATION: (14)..(14)
<223> OTHER INFORMATION: Xaa comprises any amino acid
<220> FEATURE:
<221> NAME/KEY: MISC_FEATURE
<222> LOCATION: (15)..(15)
<223> OTHER INFORMATION: Xaa comprises I or L

<400> SEQUENCE: 1

Cys Phe Xaa Xaa Xaa Xaa Asp Arg Ile Xaa Xaa Xaa Ser Xaa Xaa Gly
```

Cys

<210> SEQ ID NO 2
<211> LENGTH: 17
<212> TYPE: PRT
<213> ORGANISM: Artificial Sequence
<220> FEATURE:
<223> OTHER INFORMATION: K-ring derived 17 aa peptide #2
<220> FEATURE:
<221> NAME/KEY: MISC_FEATURE
<222> LOCATION: (3)..(3)
<223> OTHER INFORMATION: Xaa comprises D or G
<220> FEATURE:
<221> NAME/KEY: MISC_FEATURE
<222> LOCATION: (4)..(4)
<223> OTHER INFORMATION: Xaa comprises any amino acid
<220> FEATURE:
<221> NAME/KEY: MISC_FEATURE
<222> LOCATION: (5)..(5)
<223> OTHER INFORMATION: Xaa comprises R or K
<220> FEATURE:
<221> NAME/KEY: MISC_FEATURE
<222> LOCATION: (6)..(6)
<223> OTHER INFORMATION: Xaa comprises M, I or L
<220> FEATURE:
<221> NAME/KEY: MISC_FEATURE
<222> LOCATION: (10)..(10)
<223> OTHER INFORMATION: Xaa comprises G, S or N
<220> FEATURE:
<221> NAME/KEY: MISC_FEATURE
<222> LOCATION: (11)..(11)
<223> OTHER INFORMATION: Xaa comprises A, H or S
<220> FEATURE:
<221> NAME/KEY: MISC_FEATURE
<222> LOCATION: (12)..(12)
<223> OTHER INFORMATION: Xaa comprises Q, T, S, M or V
<220> FEATURE:
<221> NAME/KEY: MISC_FEATURE
<222> LOCATION: (14)..(14)
<223> OTHER INFORMATION: Xaa comprises any amino acid
<220> FEATURE:
<221> NAME/KEY: MISC_FEATURE
<222> LOCATION: (15)..(15)
<223> OTHER INFORMATION: Xaa comprises I or L

<400> SEQUENCE: 2

Cys Phe Xaa Xaa Xaa Xaa Asp Arg Ile Xaa Xaa Xaa Ser Xaa Xaa Gly
1               5                   10                  15

Cys

<210> SEQ ID NO 3
<211> LENGTH: 17
<212> TYPE: PRT
<213> ORGANISM: Artificial Sequence
<220> FEATURE:
<223> OTHER INFORMATION: K-ring derived 17 aa peptide #3
<220> FEATURE:
<221> NAME/KEY: MISC_FEATURE
<222> LOCATION: (3)..(3)
<223> OTHER INFORMATION: Xaa comprises any amino acid
<220> FEATURE:
<221> NAME/KEY: MISC_FEATURE
<222> LOCATION: (4)..(4)
<223> OTHER INFORMATION: Xaa comprises R or G
<220> FEATURE:
<221> NAME/KEY: MISC_FEATURE
<222> LOCATION: (5)..(5)
<223> OTHER INFORMATION: Xaa comprises R or K
<220> FEATURE:
<221> NAME/KEY: MISC_FEATURE
<222> LOCATION: (6)..(6)
<223> OTHER INFORMATION: Xaa comprises M, I or L
<220> FEATURE:

```
<221> NAME/KEY: MISC_FEATURE
<222> LOCATION: (10)..(10)
<223> OTHER INFORMATION: Xaa comprises G, S or N
<220> FEATURE:
<221> NAME/KEY: MISC_FEATURE
<222> LOCATION: (11)..(11)
<223> OTHER INFORMATION: Xaa comprises A, H or S
<220> FEATURE:
<221> NAME/KEY: MISC_FEATURE
<222> LOCATION: (12)..(12)
<223> OTHER INFORMATION: Xaa comprises Q, T, S, M or V
<220> FEATURE:
<221> NAME/KEY: MISC_FEATURE
<222> LOCATION: (14)..(14)
<223> OTHER INFORMATION: Xaa comprises any amino acid
<220> FEATURE:
<221> NAME/KEY: MISC_FEATURE
<222> LOCATION: (15)..(15)
<223> OTHER INFORMATION: Xaa comprises I or L

<400> SEQUENCE: 3

Cys Phe Xaa Xaa Xaa Xaa Asp Arg Ile Xaa Xaa Xaa Ser Xaa Xaa Gly
1               5                   10                  15

Cys

<210> SEQ ID NO 4
<211> LENGTH: 17
<212> TYPE: PRT
<213> ORGANISM: Artificial Sequence
<220> FEATURE:
<223> OTHER INFORMATION: K-ring derived 17 aa peptide #4
<220> FEATURE:
<221> NAME/KEY: MISC_FEATURE
<222> LOCATION: (3)..(4)
<223> OTHER INFORMATION: Xaa comprises any amino acid
<220> FEATURE:
<221> NAME/KEY: MISC_FEATURE
<222> LOCATION: (5)..(5)
<223> OTHER INFORMATION: Xaa comprises R or K
<220> FEATURE:
<221> NAME/KEY: MISC_FEATURE
<222> LOCATION: (6)..(6)
<223> OTHER INFORMATION: Xaa comprises M, I or L
<220> FEATURE:
<221> NAME/KEY: MISC_FEATURE
<222> LOCATION: (10)..(10)
<223> OTHER INFORMATION: Xaa comprises G, S or N
<220> FEATURE:
<221> NAME/KEY: MISC_FEATURE
<222> LOCATION: (11)..(11)
<223> OTHER INFORMATION: Xaa comprises A, H or S
<220> FEATURE:
<221> NAME/KEY: MISC_FEATURE
<222> LOCATION: (12)..(12)
<223> OTHER INFORMATION: Xaa comprises Q, T, S, M or V
<220> FEATURE:
<221> NAME/KEY: MISC_FEATURE
<222> LOCATION: (14)..(14)
<223> OTHER INFORMATION: Xaa comprises D or G
<220> FEATURE:
<221> NAME/KEY: MISC_FEATURE
<222> LOCATION: (15)..(15)
<223> OTHER INFORMATION: Xaa comprises I or L

<400> SEQUENCE: 4

Cys Phe Xaa Xaa Xaa Xaa Asp Arg Ile Xaa Xaa Xaa Ser Xaa Xaa Gly
1               5                   10                  15

Cys

<210> SEQ ID NO 5
<211> LENGTH: 17
<212> TYPE: PRT
<213> ORGANISM: Artificial Sequence
```

```
<220> FEATURE:
<223> OTHER INFORMATION: K-ring derived 17 aa peptide #5
<220> FEATURE:
<221> NAME/KEY: MISC_FEATURE
<222> LOCATION: (4)..(4)
<223> OTHER INFORMATION: Xaa comprises any amino acid
<220> FEATURE:
<221> NAME/KEY: MISC_FEATURE
<222> LOCATION: (5)..(5)
<223> OTHER INFORMATION: Xaa comprises R or K
<220> FEATURE:
<221> NAME/KEY: MISC_FEATURE
<222> LOCATION: (6)..(6)
<223> OTHER INFORMATION: Xaa comprises M, I or L
<220> FEATURE:
<221> NAME/KEY: MISC_FEATURE
<222> LOCATION: (10)..(10)
<223> OTHER INFORMATION: Xaa comprises G, S or N
<220> FEATURE:
<221> NAME/KEY: MISC_FEATURE
<222> LOCATION: (11)..(11)
<223> OTHER INFORMATION: Xaa comprises A, H or S
<220> FEATURE:
<221> NAME/KEY: MISC_FEATURE
<222> LOCATION: (12)..(12)
<223> OTHER INFORMATION: Xaa comprises Q, T, S, M or V
<220> FEATURE:
<221> NAME/KEY: MISC_FEATURE
<222> LOCATION: (14)..(14)
<223> OTHER INFORMATION: Xaa comprises any amino acid
<220> FEATURE:
<221> NAME/KEY: MISC_FEATURE
<222> LOCATION: (15)..(15)
<223> OTHER INFORMATION: Xaa comprises I or L

<400> SEQUENCE: 5

Cys Phe Asp Xaa Xaa Xaa Asp Arg Ile Xaa Xaa Xaa Ser Xaa Xaa Gly
1               5                   10                  15

Cys

<210> SEQ ID NO 6
<211> LENGTH: 17
<212> TYPE: PRT
<213> ORGANISM: Artificial Sequence
<220> FEATURE:
<223> OTHER INFORMATION: K-ring derived 17 aa peptide #6
<220> FEATURE:
<221> NAME/KEY: MISC_FEATURE
<222> LOCATION: (4)..(4)
<223> OTHER INFORMATION: Xaa comprises any amino acid
<220> FEATURE:
<221> NAME/KEY: MISC_FEATURE
<222> LOCATION: (5)..(5)
<223> OTHER INFORMATION: Xaa comprises R or K
<220> FEATURE:
<221> NAME/KEY: MISC_FEATURE
<222> LOCATION: (6)..(6)
<223> OTHER INFORMATION: Xaa comprises M, I or L
<220> FEATURE:
<221> NAME/KEY: MISC_FEATURE
<222> LOCATION: (10)..(10)
<223> OTHER INFORMATION: Xaa comprises G, S or N
<220> FEATURE:
<221> NAME/KEY: MISC_FEATURE
<222> LOCATION: (11)..(11)
<223> OTHER INFORMATION: Xaa comprises A, H or S
<220> FEATURE:
<221> NAME/KEY: MISC_FEATURE
<222> LOCATION: (12)..(12)
<223> OTHER INFORMATION: Xaa comprises Q, T, S, M or V
<220> FEATURE:
<221> NAME/KEY: MISC_FEATURE
<222> LOCATION: (14)..(14)
<223> OTHER INFORMATION: Xaa comprises any amino acid
<220> FEATURE:
<221> NAME/KEY: MISC_FEATURE
```

<222> LOCATION: (15)..(15)
<223> OTHER INFORMATION: Xaa comprises I or L

<400> SEQUENCE: 6

Cys Phe Gly Xaa Xaa Xaa Asp Arg Ile Xaa Xaa Xaa Ser Xaa Xaa Gly
1               5                   10                  15

Cys

<210> SEQ ID NO 7
<211> LENGTH: 17
<212> TYPE: PRT
<213> ORGANISM: Artificial Sequence
<220> FEATURE:
<223> OTHER INFORMATION: K-ring derived 17 aa peptide #7
<220> FEATURE:
<221> NAME/KEY: MISC_FEATURE
<222> LOCATION: (3)..(3)
<223> OTHER INFORMATION: Xaa comprises any amino acid
<220> FEATURE:
<221> NAME/KEY: MISC_FEATURE
<222> LOCATION: (5)..(5)
<223> OTHER INFORMATION: Xaa comprises R or K
<220> FEATURE:
<221> NAME/KEY: MISC_FEATURE
<222> LOCATION: (6)..(6)
<223> OTHER INFORMATION: Xaa comprises M, I or L
<220> FEATURE:
<221> NAME/KEY: MISC_FEATURE
<222> LOCATION: (10)..(10)
<223> OTHER INFORMATION: Xaa comprises G, S or N
<220> FEATURE:
<221> NAME/KEY: MISC_FEATURE
<222> LOCATION: (11)..(11)
<223> OTHER INFORMATION: Xaa comprises A, H or S
<220> FEATURE:
<221> NAME/KEY: MISC_FEATURE
<222> LOCATION: (12)..(12)
<223> OTHER INFORMATION: Xaa comprises Q, T, S, M or V
<220> FEATURE:
<221> NAME/KEY: MISC_FEATURE
<222> LOCATION: (14)..(14)
<223> OTHER INFORMATION: Xaa comprises any amino acid
<220> FEATURE:
<221> NAME/KEY: MISC_FEATURE
<222> LOCATION: (15)..(15)
<223> OTHER INFORMATION: Xaa comprises I or L

<400> SEQUENCE: 7

Cys Phe Xaa Arg Xaa Xaa Asp Arg Ile Xaa Xaa Xaa Ser Xaa Xaa Gly
1               5                   10                  15

Cys

<210> SEQ ID NO 8
<211> LENGTH: 17
<212> TYPE: PRT
<213> ORGANISM: Artificial Sequence
<220> FEATURE:
<223> OTHER INFORMATION: K-ring derived 17 aa peptide #8
<220> FEATURE:
<221> NAME/KEY: MISC_FEATURE
<222> LOCATION: (3)..(3)
<223> OTHER INFORMATION: Xaa comprises any amino acid
<220> FEATURE:
<221> NAME/KEY: MISC_FEATURE
<222> LOCATION: (5)..(5)
<223> OTHER INFORMATION: Xaa comprises R or K
<220> FEATURE:
<221> NAME/KEY: MISC_FEATURE
<222> LOCATION: (6)..(6)
<223> OTHER INFORMATION: Xaa comprises M, I or L
<220> FEATURE:
<221> NAME/KEY: MISC_FEATURE
<222> LOCATION: (10)..(10)

```
<223> OTHER INFORMATION: Xaa comprises G, S or N
<220> FEATURE:
<221> NAME/KEY: MISC_FEATURE
<222> LOCATION: (11)..(11)
<223> OTHER INFORMATION: Xaa comprises A, H or S
<220> FEATURE:
<221> NAME/KEY: MISC_FEATURE
<222> LOCATION: (12)..(12)
<223> OTHER INFORMATION: Xaa comprises Q, T, S, M or V
<220> FEATURE:
<221> NAME/KEY: MISC_FEATURE
<222> LOCATION: (14)..(14)
<223> OTHER INFORMATION: Xaa comprises any amino acid
<220> FEATURE:
<221> NAME/KEY: MISC_FEATURE
<222> LOCATION: (15)..(15)
<223> OTHER INFORMATION: Xaa comprises I or L

<400> SEQUENCE: 8

Cys Phe Xaa Gly Xaa Xaa Asp Arg Ile Xaa Xaa Xaa Ser Xaa Xaa Gly
1               5                   10                  15

Cys

<210> SEQ ID NO 9
<211> LENGTH: 17
<212> TYPE: PRT
<213> ORGANISM: Artificial Sequence
<220> FEATURE:
<223> OTHER INFORMATION: K-ring derived 17 aa peptide #9
<220> FEATURE:
<221> NAME/KEY: MISC_FEATURE
<222> LOCATION: (3)..(4)
<223> OTHER INFORMATION: Xaa comprises any amino acid
<220> FEATURE:
<221> NAME/KEY: MISC_FEATURE
<222> LOCATION: (5)..(5)
<223> OTHER INFORMATION: Xaa comprises R or K
<220> FEATURE:
<221> NAME/KEY: MISC_FEATURE
<222> LOCATION: (6)..(6)
<223> OTHER INFORMATION: Xaa comprises M, I or L
<220> FEATURE:
<221> NAME/KEY: MISC_FEATURE
<222> LOCATION: (10)..(10)
<223> OTHER INFORMATION: Xaa comprises G, S or N
<220> FEATURE:
<221> NAME/KEY: MISC_FEATURE
<222> LOCATION: (11)..(11)
<223> OTHER INFORMATION: Xaa comprises A, H or S
<220> FEATURE:
<221> NAME/KEY: MISC_FEATURE
<222> LOCATION: (12)..(12)
<223> OTHER INFORMATION: Xaa comprises Q, T, S, M or V
<220> FEATURE:
<221> NAME/KEY: MISC_FEATURE
<222> LOCATION: (15)..(15)
<223> OTHER INFORMATION: Xaa comprises I or L

<400> SEQUENCE: 9

Cys Phe Xaa Xaa Xaa Xaa Asp Arg Ile Xaa Xaa Xaa Ser Asp Xaa Gly
1               5                   10                  15

Cys

<210> SEQ ID NO 10
<211> LENGTH: 17
<212> TYPE: PRT
<213> ORGANISM: Artificial Sequence
<220> FEATURE:
<223> OTHER INFORMATION: K-ring derived 17 aa peptide #10
<220> FEATURE:
<221> NAME/KEY: MISC_FEATURE
<222> LOCATION: (3)..(4)
<223> OTHER INFORMATION: Xaa comprises any amino acid
```

-continued

```
<220> FEATURE:
<221> NAME/KEY: MISC_FEATURE
<222> LOCATION: (5)..(5)
<223> OTHER INFORMATION: Xaa comprises R or K
<220> FEATURE:
<221> NAME/KEY: MISC_FEATURE
<222> LOCATION: (6)..(6)
<223> OTHER INFORMATION: Xaa comprises M, I or L
<220> FEATURE:
<221> NAME/KEY: MISC_FEATURE
<222> LOCATION: (10)..(10)
<223> OTHER INFORMATION: Xaa comprises G, S or N
<220> FEATURE:
<221> NAME/KEY: MISC_FEATURE
<222> LOCATION: (11)..(11)
<223> OTHER INFORMATION: Xaa comprises A, H or S
<220> FEATURE:
<221> NAME/KEY: MISC_FEATURE
<222> LOCATION: (12)..(12)
<223> OTHER INFORMATION: Xaa comprises Q, T, S, M or V
<220> FEATURE:
<221> NAME/KEY: MISC_FEATURE
<222> LOCATION: (15)..(15)
<223> OTHER INFORMATION: Xaa comprises I or L

<400> SEQUENCE: 10

Cys Phe Xaa Xaa Xaa Xaa Asp Arg Ile Xaa Xaa Xaa Ser Gly Xaa Gly
1               5                   10                  15

Cys

<210> SEQ ID NO 11
<211> LENGTH: 17
<212> TYPE: PRT
<213> ORGANISM: Artificial Sequence
<220> FEATURE:
<223> OTHER INFORMATION: K-ring derived 17 aa peptide #11
<220> FEATURE:
<221> NAME/KEY: MISC_FEATURE
<222> LOCATION: (5)..(5)
<223> OTHER INFORMATION: Xaa comprises R or K
<220> FEATURE:
<221> NAME/KEY: MISC_FEATURE
<222> LOCATION: (6)..(6)
<223> OTHER INFORMATION: Xaa comprises M, I or L
<220> FEATURE:
<221> NAME/KEY: MISC_FEATURE
<222> LOCATION: (10)..(10)
<223> OTHER INFORMATION: Xaa comprises G, S or N
<220> FEATURE:
<221> NAME/KEY: MISC_FEATURE
<222> LOCATION: (11)..(11)
<223> OTHER INFORMATION: Xaa comprises A, H or S
<220> FEATURE:
<221> NAME/KEY: MISC_FEATURE
<222> LOCATION: (12)..(12)
<223> OTHER INFORMATION: Xaa comprises Q, T, S, M or V
<220> FEATURE:
<221> NAME/KEY: MISC_FEATURE
<222> LOCATION: (14)..(14)
<223> OTHER INFORMATION: Xaa comprises any amino acid
<220> FEATURE:
<221> NAME/KEY: MISC_FEATURE
<222> LOCATION: (15)..(15)
<223> OTHER INFORMATION: Xaa comprises I or L

<400> SEQUENCE: 11

Cys Phe Asp Arg Xaa Xaa Asp Arg Ile Xaa Xaa Xaa Ser Xaa Xaa Gly
1               5                   10                  15

Cys

<210> SEQ ID NO 12
<211> LENGTH: 17
<212> TYPE: PRT
```

```
<213> ORGANISM: Artificial Sequence
<220> FEATURE:
<223> OTHER INFORMATION: K-ring derived 17 aa peptide #12
<220> FEATURE:
<221> NAME/KEY: MISC_FEATURE
<222> LOCATION: (5)..(5)
<223> OTHER INFORMATION: Xaa comprises R or K
<220> FEATURE:
<221> NAME/KEY: MISC_FEATURE
<222> LOCATION: (6)..(6)
<223> OTHER INFORMATION: Xaa comprises M, I or L
<220> FEATURE:
<221> NAME/KEY: MISC_FEATURE
<222> LOCATION: (10)..(10)
<223> OTHER INFORMATION: Xaa comprises G, S or N
<220> FEATURE:
<221> NAME/KEY: MISC_FEATURE
<222> LOCATION: (11)..(11)
<223> OTHER INFORMATION: Xaa comprises A, H or S
<220> FEATURE:
<221> NAME/KEY: MISC_FEATURE
<222> LOCATION: (12)..(12)
<223> OTHER INFORMATION: Xaa comprises Q, T, S, M or V
<220> FEATURE:
<221> NAME/KEY: MISC_FEATURE
<222> LOCATION: (14)..(14)
<223> OTHER INFORMATION: Xaa comprises any amino acid
<220> FEATURE:
<221> NAME/KEY: MISC_FEATURE
<222> LOCATION: (15)..(15)
<223> OTHER INFORMATION: Xaa comprises I or L

<400> SEQUENCE: 12

Cys Phe Gly Arg Xaa Xaa Asp Arg Ile Xaa Xaa Xaa Ser Xaa Xaa Gly
1               5                   10                  15

Cys

<210> SEQ ID NO 13
<211> LENGTH: 17
<212> TYPE: PRT
<213> ORGANISM: Artificial Sequence
<220> FEATURE:
<223> OTHER INFORMATION: K-ring derived 17 aa peptide #13
<220> FEATURE:
<221> NAME/KEY: MISC_FEATURE
<222> LOCATION: (5)..(5)
<223> OTHER INFORMATION: Xaa comprises R or K
<220> FEATURE:
<221> NAME/KEY: MISC_FEATURE
<222> LOCATION: (6)..(6)
<223> OTHER INFORMATION: Xaa comprises M, I or L
<220> FEATURE:
<221> NAME/KEY: MISC_FEATURE
<222> LOCATION: (10)..(10)
<223> OTHER INFORMATION: Xaa comprises G, S or N
<220> FEATURE:
<221> NAME/KEY: MISC_FEATURE
<222> LOCATION: (11)..(11)
<223> OTHER INFORMATION: Xaa comprises A, H or S
<220> FEATURE:
<221> NAME/KEY: MISC_FEATURE
<222> LOCATION: (12)..(12)
<223> OTHER INFORMATION: Xaa comprises Q, T, S, M or V
<220> FEATURE:
<221> NAME/KEY: MISC_FEATURE
<222> LOCATION: (14)..(14)
<223> OTHER INFORMATION: Xaa comprises any amino acid
<220> FEATURE:
<221> NAME/KEY: MISC_FEATURE
<222> LOCATION: (15)..(15)
<223> OTHER INFORMATION: Xaa comprises I or L

<400> SEQUENCE: 13

Cys Phe Asp Gly Xaa Xaa Asp Arg Ile Xaa Xaa Xaa Ser Xaa Xaa Gly
1               5                   10                  15
```

Cys

```
<210> SEQ ID NO 14
<211> LENGTH: 17
<212> TYPE: PRT
<213> ORGANISM: Artificial Sequence
<220> FEATURE:
<223> OTHER INFORMATION: K-ring derived 17 aa peptide #14
<220> FEATURE:
<221> NAME/KEY: MISC_FEATURE
<222> LOCATION: (5)..(5)
<223> OTHER INFORMATION: Xaa comprises R or K
<220> FEATURE:
<221> NAME/KEY: MISC_FEATURE
<222> LOCATION: (6)..(6)
<223> OTHER INFORMATION: Xaa comprises M, I or L
<220> FEATURE:
<221> NAME/KEY: MISC_FEATURE
<222> LOCATION: (10)..(10)
<223> OTHER INFORMATION: Xaa comprises G, S or N
<220> FEATURE:
<221> NAME/KEY: MISC_FEATURE
<222> LOCATION: (11)..(11)
<223> OTHER INFORMATION: Xaa comprises A, H or S
<220> FEATURE:
<221> NAME/KEY: MISC_FEATURE
<222> LOCATION: (12)..(12)
<223> OTHER INFORMATION: Xaa comprises Q, T, S, M or V
<220> FEATURE:
<221> NAME/KEY: MISC_FEATURE
<222> LOCATION: (14)..(14)
<223> OTHER INFORMATION: Xaa comprises any amino acid
<220> FEATURE:
<221> NAME/KEY: MISC_FEATURE
<222> LOCATION: (15)..(15)
<223> OTHER INFORMATION: Xaa comprises I or L

<400> SEQUENCE: 14

Cys Phe Gly Gly Xaa Xaa Asp Arg Ile Xaa Xaa Xaa Ser Xaa Xaa Gly
1               5                   10                  15

Cys

<210> SEQ ID NO 15
<211> LENGTH: 17
<212> TYPE: PRT
<213> ORGANISM: Artificial Sequence
<220> FEATURE:
<223> OTHER INFORMATION: K-ring derived 17 aa peptide #15
<220> FEATURE:
<221> NAME/KEY: MISC_FEATURE
<222> LOCATION: (4)..(4)
<223> OTHER INFORMATION: Xaa comprises any amino acid
<220> FEATURE:
<221> NAME/KEY: MISC_FEATURE
<222> LOCATION: (5)..(5)
<223> OTHER INFORMATION: Xaa comprises R or K
<220> FEATURE:
<221> NAME/KEY: MISC_FEATURE
<222> LOCATION: (6)..(6)
<223> OTHER INFORMATION: Xaa comprises M, I or L
<220> FEATURE:
<221> NAME/KEY: MISC_FEATURE
<222> LOCATION: (10)..(10)
<223> OTHER INFORMATION: Xaa comprises G, S or N
<220> FEATURE:
<221> NAME/KEY: MISC_FEATURE
<222> LOCATION: (11)..(11)
<223> OTHER INFORMATION: Xaa comprises A, H or S
<220> FEATURE:
<221> NAME/KEY: MISC_FEATURE
<222> LOCATION: (12)..(12)
<223> OTHER INFORMATION: Xaa comprises Q, T, S, M or V
<220> FEATURE:
<221> NAME/KEY: MISC_FEATURE
```

<222> LOCATION: (15)..(15)
<223> OTHER INFORMATION: Xaa comprises I or L

<400> SEQUENCE: 15

Cys Phe Asp Xaa Xaa Xaa Asp Arg Ile Xaa Xaa Xaa Ser Asp Xaa Gly
1               5                   10                  15

Cys

<210> SEQ ID NO 16
<211> LENGTH: 17
<212> TYPE: PRT
<213> ORGANISM: Artificial Sequence
<220> FEATURE:
<223> OTHER INFORMATION: K-ring derived 17 aa peptide #16
<220> FEATURE:
<221> NAME/KEY: MISC_FEATURE
<222> LOCATION: (4)..(4)
<223> OTHER INFORMATION: Xaa comprises any amino acid
<220> FEATURE:
<221> NAME/KEY: MISC_FEATURE
<222> LOCATION: (5)..(5)
<223> OTHER INFORMATION: Xaa comprises R or K
<220> FEATURE:
<221> NAME/KEY: MISC_FEATURE
<222> LOCATION: (6)..(6)
<223> OTHER INFORMATION: Xaa comprises M, I or L
<220> FEATURE:
<221> NAME/KEY: MISC_FEATURE
<222> LOCATION: (10)..(10)
<223> OTHER INFORMATION: Xaa comprises G, S or N
<220> FEATURE:
<221> NAME/KEY: MISC_FEATURE
<222> LOCATION: (11)..(11)
<223> OTHER INFORMATION: Xaa comprises A, H or S
<220> FEATURE:
<221> NAME/KEY: MISC_FEATURE
<222> LOCATION: (12)..(12)
<223> OTHER INFORMATION: Xaa comprises Q, T, S, M or V
<220> FEATURE:
<221> NAME/KEY: MISC_FEATURE
<222> LOCATION: (15)..(15)
<223> OTHER INFORMATION: Xaa comprises I or L

<400> SEQUENCE: 16

Cys Phe Gly Xaa Xaa Xaa Asp Arg Ile Xaa Xaa Xaa Ser Asp Xaa Gly
1               5                   10                  15

Cys

<210> SEQ ID NO 17
<211> LENGTH: 17
<212> TYPE: PRT
<213> ORGANISM: Artificial Sequence
<220> FEATURE:
<223> OTHER INFORMATION: K-ring derived 17 aa peptide #17
<220> FEATURE:
<221> NAME/KEY: MISC_FEATURE
<222> LOCATION: (4)..(4)
<223> OTHER INFORMATION: Xaa comprises any amino acid
<220> FEATURE:
<221> NAME/KEY: MISC_FEATURE
<222> LOCATION: (5)..(5)
<223> OTHER INFORMATION: Xaa comprises R or K
<220> FEATURE:
<221> NAME/KEY: MISC_FEATURE
<222> LOCATION: (6)..(6)
<223> OTHER INFORMATION: Xaa comprises M, I or L
<220> FEATURE:
<221> NAME/KEY: MISC_FEATURE
<222> LOCATION: (10)..(10)
<223> OTHER INFORMATION: Xaa comprises G, S or N
<220> FEATURE:
<221> NAME/KEY: MISC_FEATURE
<222> LOCATION: (11)..(11)

<223> OTHER INFORMATION: Xaa comprises A, H or S
<220> FEATURE:
<221> NAME/KEY: MISC_FEATURE
<222> LOCATION: (12)..(12)
<223> OTHER INFORMATION: Xaa comprises Q, T, S, M or V
<220> FEATURE:
<221> NAME/KEY: MISC_FEATURE
<222> LOCATION: (15)..(15)
<223> OTHER INFORMATION: Xaa comprises I or L

<400> SEQUENCE: 17

Cys Phe Asp Xaa Xaa Xaa Asp Arg Ile Xaa Xaa Xaa Ser Gly Xaa Gly
1               5                   10                  15
Cys

<210> SEQ ID NO 18
<211> LENGTH: 17
<212> TYPE: PRT
<213> ORGANISM: Artificial Sequence
<220> FEATURE:
<223> OTHER INFORMATION: K-ring derived 17 aa peptide #18
<220> FEATURE:
<221> NAME/KEY: MISC_FEATURE
<222> LOCATION: (4)..(4)
<223> OTHER INFORMATION: Xaa comprises any amino acid
<220> FEATURE:
<221> NAME/KEY: MISC_FEATURE
<222> LOCATION: (5)..(5)
<223> OTHER INFORMATION: Xaa comprises R or K
<220> FEATURE:
<221> NAME/KEY: MISC_FEATURE
<222> LOCATION: (6)..(6)
<223> OTHER INFORMATION: Xaa comprises M, I or L
<220> FEATURE:
<221> NAME/KEY: MISC_FEATURE
<222> LOCATION: (10)..(10)
<223> OTHER INFORMATION: Xaa comprises G, S or N
<220> FEATURE:
<221> NAME/KEY: MISC_FEATURE
<222> LOCATION: (11)..(11)
<223> OTHER INFORMATION: Xaa comprises A, H or S
<220> FEATURE:
<221> NAME/KEY: MISC_FEATURE
<222> LOCATION: (12)..(12)
<223> OTHER INFORMATION: Xaa comprises Q, T, S, M or V
<220> FEATURE:
<221> NAME/KEY: MISC_FEATURE
<222> LOCATION: (15)..(15)
<223> OTHER INFORMATION: Xaa comprises I or L

<400> SEQUENCE: 18

Cys Phe Gly Xaa Xaa Xaa Asp Arg Ile Xaa Xaa Xaa Ser Gly Xaa Gly
1               5                   10                  15
Cys

<210> SEQ ID NO 19
<211> LENGTH: 17
<212> TYPE: PRT
<213> ORGANISM: Artificial Sequence
<220> FEATURE:
<223> OTHER INFORMATION: K-ring derived 17 aa peptide #19
<220> FEATURE:
<221> NAME/KEY: MISC_FEATURE
<222> LOCATION: (3)..(3)
<223> OTHER INFORMATION: Xaa comprises any amino acid
<220> FEATURE:
<221> NAME/KEY: MISC_FEATURE
<222> LOCATION: (5)..(5)
<223> OTHER INFORMATION: Xaa comprises R or K
<220> FEATURE:
<221> NAME/KEY: MISC_FEATURE
<222> LOCATION: (6)..(6)
<223> OTHER INFORMATION: Xaa comprises M, I or L -continued

```
<220> FEATURE:
<221> NAME/KEY: MISC_FEATURE
<222> LOCATION: (10)..(10)
<223> OTHER INFORMATION: Xaa comprises G, S or N
<220> FEATURE:
<221> NAME/KEY: MISC_FEATURE
<222> LOCATION: (11)..(11)
<223> OTHER INFORMATION: Xaa comprises A, H or S
<220> FEATURE:
<221> NAME/KEY: MISC_FEATURE
<222> LOCATION: (12)..(12)
<223> OTHER INFORMATION: Xaa comprises Q, T, S, M or V
<220> FEATURE:
<221> NAME/KEY: MISC_FEATURE
<222> LOCATION: (15)..(15)
<223> OTHER INFORMATION: Xaa comprises I or L

<400> SEQUENCE: 19

Cys Phe Xaa Arg Xaa Xaa Asp Arg Ile Xaa Xaa Xaa Ser Asp Xaa Gly
1               5                   10                  15

Cys

<210> SEQ ID NO 20
<211> LENGTH: 17
<212> TYPE: PRT
<213> ORGANISM: Artificial Sequence
<220> FEATURE:
<223> OTHER INFORMATION: K-ring derived 17 aa peptide #20
<220> FEATURE:
<221> NAME/KEY: MISC_FEATURE
<222> LOCATION: (3)..(3)
<223> OTHER INFORMATION: Xaa comprises any amino acid
<220> FEATURE:
<221> NAME/KEY: MISC_FEATURE
<222> LOCATION: (5)..(5)
<223> OTHER INFORMATION: Xaa comprises R or K
<220> FEATURE:
<221> NAME/KEY: MISC_FEATURE
<222> LOCATION: (6)..(6)
<223> OTHER INFORMATION: Xaa comprises M, I or L
<220> FEATURE:
<221> NAME/KEY: MISC_FEATURE
<222> LOCATION: (10)..(10)
<223> OTHER INFORMATION: Xaa comprises G, S or N
<220> FEATURE:
<221> NAME/KEY: MISC_FEATURE
<222> LOCATION: (11)..(11)
<223> OTHER INFORMATION: Xaa comprises A, H or S
<220> FEATURE:
<221> NAME/KEY: MISC_FEATURE
<222> LOCATION: (12)..(12)
<223> OTHER INFORMATION: Xaa comprises Q, T, S, M or V
<220> FEATURE:
<221> NAME/KEY: MISC_FEATURE
<222> LOCATION: (15)..(15)
<223> OTHER INFORMATION: Xaa comprises I or L

<400> SEQUENCE: 20

Cys Phe Xaa Arg Xaa Xaa Asp Arg Ile Xaa Xaa Xaa Ser Gly Xaa Gly
1               5                   10                  15

Cys

<210> SEQ ID NO 21
<211> LENGTH: 17
<212> TYPE: PRT
<213> ORGANISM: Artificial Sequence
<220> FEATURE:
<223> OTHER INFORMATION: K-ring derived 17 aa peptide #21
<220> FEATURE:
<221> NAME/KEY: MISC_FEATURE
<222> LOCATION: (3)..(3)
<223> OTHER INFORMATION: Xaa comprises any amino acid
<220> FEATURE:
```

```
<221> NAME/KEY: MISC_FEATURE
<222> LOCATION: (5)..(5)
<223> OTHER INFORMATION: Xaa comprises R or K
<220> FEATURE:
<221> NAME/KEY: MISC_FEATURE
<222> LOCATION: (6)..(6)
<223> OTHER INFORMATION: Xaa comprises M, I or L
<220> FEATURE:
<221> NAME/KEY: MISC_FEATURE
<222> LOCATION: (10)..(10)
<223> OTHER INFORMATION: Xaa comprises G, S or N
<220> FEATURE:
<221> NAME/KEY: MISC_FEATURE
<222> LOCATION: (11)..(11)
<223> OTHER INFORMATION: Xaa comprises A, H or S
<220> FEATURE:
<221> NAME/KEY: MISC_FEATURE
<222> LOCATION: (12)..(12)
<223> OTHER INFORMATION: Xaa comprises Q, T, S, M or V
<220> FEATURE:
<221> NAME/KEY: MISC_FEATURE
<222> LOCATION: (15)..(15)
<223> OTHER INFORMATION: Xaa comprises I or L

<400> SEQUENCE: 21

Cys Phe Xaa Gly Xaa Xaa Asp Arg Ile Xaa Xaa Xaa Ser Asp Xaa Gly
1               5                   10                  15

Cys

<210> SEQ ID NO 22
<211> LENGTH: 17
<212> TYPE: PRT
<213> ORGANISM: Artificial Sequence
<220> FEATURE:
<223> OTHER INFORMATION: K-ring derived 17 aa peptide #22
<220> FEATURE:
<221> NAME/KEY: MISC_FEATURE
<222> LOCATION: (3)..(3)
<223> OTHER INFORMATION: Xaa comprises any amino acid
<220> FEATURE:
<221> NAME/KEY: MISC_FEATURE
<222> LOCATION: (5)..(5)
<223> OTHER INFORMATION: Xaa comprises R or K
<220> FEATURE:
<221> NAME/KEY: MISC_FEATURE
<222> LOCATION: (6)..(6)
<223> OTHER INFORMATION: Xaa comprises M, I or L
<220> FEATURE:
<221> NAME/KEY: MISC_FEATURE
<222> LOCATION: (10)..(10)
<223> OTHER INFORMATION: Xaa comprises G, S or N
<220> FEATURE:
<221> NAME/KEY: MISC_FEATURE
<222> LOCATION: (11)..(11)
<223> OTHER INFORMATION: Xaa comprises A, H or S
<220> FEATURE:
<221> NAME/KEY: MISC_FEATURE
<222> LOCATION: (12)..(12)
<223> OTHER INFORMATION: Xaa comprises Q, T, S, M or V
<220> FEATURE:
<221> NAME/KEY: MISC_FEATURE
<222> LOCATION: (15)..(15)
<223> OTHER INFORMATION: Xaa comprises I or L

<400> SEQUENCE: 22

Cys Phe Xaa Gly Xaa Xaa Asp Arg Ile Xaa Xaa Xaa Ser Gly Xaa Gly
1               5                   10                  15

Cys

<210> SEQ ID NO 23
<211> LENGTH: 22
<212> TYPE: PRT
<213> ORGANISM: Artificial Sequence
```

```
<220> FEATURE:
<223> OTHER INFORMATION: K-ring derived 22 aa peptide #23
<220> FEATURE:
<221> NAME/KEY: MISC_FEATURE
<222> LOCATION: (3)..(4)
<223> OTHER INFORMATION: Xaa comprises any amino acid
<220> FEATURE:
<221> NAME/KEY: MISC_FEATURE
<222> LOCATION: (5)..(5)
<223> OTHER INFORMATION: Xaa comprises R or K
<220> FEATURE:
<221> NAME/KEY: MISC_FEATURE
<222> LOCATION: (6)..(6)
<223> OTHER INFORMATION: Xaa comprises M, I or L
<220> FEATURE:
<221> NAME/KEY: MISC_FEATURE
<222> LOCATION: (10)..(10)
<223> OTHER INFORMATION: Xaa comprises G, S or N
<220> FEATURE:
<221> NAME/KEY: MISC_FEATURE
<222> LOCATION: (11)..(11)
<223> OTHER INFORMATION: Xaa comprises A, H or S
<220> FEATURE:
<221> NAME/KEY: MISC_FEATURE
<222> LOCATION: (12)..(12)
<223> OTHER INFORMATION: Xaa comprises Q, T, S, M or V
<220> FEATURE:
<221> NAME/KEY: MISC_FEATURE
<222> LOCATION: (14)..(14)
<223> OTHER INFORMATION: Xaa comprises any amino acid
<220> FEATURE:
<221> NAME/KEY: MISC_FEATURE
<222> LOCATION: (15)..(15)
<223> OTHER INFORMATION: Xaa comprises I or L

<400> SEQUENCE: 23

Cys Phe Xaa Xaa Xaa Xaa Asp Arg Ile Xaa Xaa Xaa Ser Xaa Xaa Gly
1               5                   10                  15

Cys Asn Ser Phe Arg Tyr
            20

<210> SEQ ID NO 24
<211> LENGTH: 17
<212> TYPE: PRT
<213> ORGANISM: Artificial Sequence
<220> FEATURE:
<223> OTHER INFORMATION: K-ring derived 17 aa peptide #24

<400> SEQUENCE: 24

Cys Phe Asp Arg Arg Ile Asp Arg Ile Ser His Thr Ser Asp Ile Gly
1               5                   10                  15

Cys

<210> SEQ ID NO 25
<211> LENGTH: 17
<212> TYPE: PRT
<213> ORGANISM: Artificial Sequence
<220> FEATURE:
<223> OTHER INFORMATION: K-ring derived 17 aa peptide #25

<400> SEQUENCE: 25

Cys Phe Gly Arg Arg Ile Asp Arg Ile Ser His Thr Ser Asp Ile Gly
1               5                   10                  15

Cys

<210> SEQ ID NO 26
<211> LENGTH: 17
<212> TYPE: PRT
<213> ORGANISM: Artificial Sequence
<220> FEATURE:
```

<223> OTHER INFORMATION: K-ring derived 17 aa peptide #26

<400> SEQUENCE: 26

Cys Phe Asp Gly Arg Ile Asp Arg Ile Ser His Thr Ser Asp Ile Gly
1               5                   10                  15

Cys

<210> SEQ ID NO 27
<211> LENGTH: 17
<212> TYPE: PRT
<213> ORGANISM: Artificial Sequence
<220> FEATURE:
<223> OTHER INFORMATION: K-ring derived 17 aa peptide #27

<400> SEQUENCE: 27

Cys Phe Asp Arg Arg Ile Asp Arg Ile Ser His Thr Ser Gly Ile Gly
1               5                   10                  15

Cys

<210> SEQ ID NO 28
<211> LENGTH: 17
<212> TYPE: PRT
<213> ORGANISM: Artificial Sequence
<220> FEATURE:
<223> OTHER INFORMATION: K-ring derived 17 aa peptide #28

<400> SEQUENCE: 28

Cys Phe Gly Gly Arg Ile Asp Arg Ile Ser His Thr Ser Asp Ile Gly
1               5                   10                  15

Cys

<210> SEQ ID NO 29
<211> LENGTH: 17
<212> TYPE: PRT
<213> ORGANISM: Artificial Sequence
<220> FEATURE:
<223> OTHER INFORMATION: K-ring derived 17 aa peptide #29

<400> SEQUENCE: 29

Cys Phe Gly Arg Arg Ile Asp Arg Ile Ser His Thr Ser Gly Ile Gly
1               5                   10                  15

Cys

<210> SEQ ID NO 30
<211> LENGTH: 17
<212> TYPE: PRT
<213> ORGANISM: Artificial Sequence
<220> FEATURE:
<223> OTHER INFORMATION: K-ring derived 17 aa peptide #30

<400> SEQUENCE: 30

Cys Phe Asp Gly Arg Ile Asp Arg Ile Ser His Thr Ser Gly Ile Gly
1               5                   10                  15

Cys

<210> SEQ ID NO 31
<211> LENGTH: 17
<212> TYPE: PRT
<213> ORGANISM: Artificial Sequence
<220> FEATURE:
<223> OTHER INFORMATION: K-ring derived 17 aa peptide #31

<400> SEQUENCE: 31

Cys Phe Gly Gly Arg Ile Asp Arg Ile Ser His Thr Ser Gly Ile Gly
1               5                   10                  15

Cys

<210> SEQ ID NO 32
<211> LENGTH: 24
<212> TYPE: PRT
<213> ORGANISM: Artificial Sequence
<220> FEATURE:
<223> OTHER INFORMATION: KNP derived peptide #1

<400> SEQUENCE: 32

Gly Leu Leu Ile Ser Cys Phe Asp Arg Arg Ile Asp Arg Ile Ser His
1               5                   10                  15

Thr Ser Asp Ile Gly Cys Arg His
            20

<210> SEQ ID NO 33
<211> LENGTH: 24
<212> TYPE: PRT
<213> ORGANISM: Artificial Sequence
<220> FEATURE:
<223> OTHER INFORMATION: KNP derived peptide #2

<400> SEQUENCE: 33

Gly Leu Leu Ile Ser Cys Phe Asp Arg Arg Ile Asp Arg Ile Ser His
1               5                   10                  15

Thr Ser Gly Ile Gly Cys Arg His
            20

<210> SEQ ID NO 34
<211> LENGTH: 24
<212> TYPE: PRT
<213> ORGANISM: Artificial Sequence
<220> FEATURE:
<223> OTHER INFORMATION: KNP derived peptide #3

<400> SEQUENCE: 34

Gly Leu Leu Ile Ser Cys Phe Gly Arg Arg Ile Asp Arg Ile Ser His
1               5                   10                  15

Thr Ser Asp Ile Gly Cys Arg His
            20

<210> SEQ ID NO 35
<211> LENGTH: 24
<212> TYPE: PRT
<213> ORGANISM: Artificial Sequence
<220> FEATURE:
<223> OTHER INFORMATION: KNP derived peptide #4

<400> SEQUENCE: 35

Gly Leu Leu Ile Ser Cys Phe Asp Gly Arg Ile Asp Arg Ile Ser His
1               5                   10                  15

Thr Ser Asp Ile Gly Cys Arg His
            20

<210> SEQ ID NO 36
<211> LENGTH: 24
<212> TYPE: PRT
<213> ORGANISM: Artificial Sequence
<220> FEATURE:
<223> OTHER INFORMATION: KNP derived peptide #5

<400> SEQUENCE: 36

```
Gly Leu Leu Ile Ser Cys Phe Gly Arg Arg Ile Asp Arg Ile Ser His
1               5                   10                  15

Thr Ser Gly Ile Gly Cys Arg His
            20
```

<210> SEQ ID NO 37
<211> LENGTH: 27
<212> TYPE: PRT
<213> ORGANISM: Artificial Sequence
<220> FEATURE:
<223> OTHER INFORMATION: KNP derived peptide #6

<400> SEQUENCE: 37

```
Gly Leu Leu Ile Ser Cys Phe Asp Arg Arg Ile Asp Arg Ile Ser His
1               5                   10                  15

Thr Ser Asp Ile Gly Cys Asn Ser Phe Arg Tyr
            20                  25
```

<210> SEQ ID NO 38
<211> LENGTH: 60
<212> TYPE: PRT
<213> ORGANISM: Artificial Sequence
<220> FEATURE:
<223> OTHER INFORMATION: KNP derived peptide #7

<400> SEQUENCE: 38

```
Gly Leu Leu Ile Ser Cys Phe Gly Arg Arg Ile Asp Arg Ile Ser His
1               5                   10                  15

Thr Ser Asp Ile Gly Cys Arg His Arg Lys Asp Pro Pro Arg Ala Pro
            20                  25                  30

Pro Ala Ala Pro Ser Ala Ala Pro Leu Ala Val Thr Trp Leu Ile Arg
        35                  40                  45

Asp Leu Arg Ala Asp Ser Lys Gln Ser Arg Ala Ala
    50                  55                  60
```

<210> SEQ ID NO 39
<211> LENGTH: 60
<212> TYPE: PRT
<213> ORGANISM: Artificial Sequence
<220> FEATURE:
<223> OTHER INFORMATION: KNP derived peptide #8

<400> SEQUENCE: 39

```
Gly Leu Leu Ile Ser Cys Phe Asp Gly Arg Ile Asp Arg Ile Ser His
1               5                   10                  15

Thr Ser Asp Ile Gly Cys Arg His Arg Lys Asp Pro Pro Arg Ala Pro
            20                  25                  30

Pro Ala Ala Pro Ser Ala Ala Pro Leu Ala Val Thr Trp Leu Ile Arg
        35                  40                  45

Asp Leu Arg Ala Asp Ser Lys Gln Ser Arg Ala Ala
    50                  55                  60
```

<210> SEQ ID NO 40
<211> LENGTH: 60
<212> TYPE: PRT
<213> ORGANISM: Artificial Sequence
<220> FEATURE:
<223> OTHER INFORMATION: KNP derived peptide #9

<400> SEQUENCE: 40

```
Gly Leu Leu Ile Ser Cys Phe Asp Arg Arg Ile Asp Arg Ile Ser His
1               5                   10                  15
```

Thr Ser Gly Ile Gly Cys Arg His Arg Lys Asp Pro Pro Arg Ala Pro
                20                  25                  30

Pro Ala Ala Pro Ser Ala Ala Pro Leu Ala Val Thr Trp Leu Ile Arg
            35                  40                  45

Asp Leu Arg Ala Asp Ser Lys Gln Ser Arg Ala Ala
        50                  55                  60

<210> SEQ ID NO 41
<211> LENGTH: 60
<212> TYPE: PRT
<213> ORGANISM: Artificial Sequence
<220> FEATURE:
<223> OTHER INFORMATION: KNP derived peptide #10

<400> SEQUENCE: 41

Gly Leu Leu Ile Ser Cys Phe Gly Gly Arg Ile Asp Arg Ile Ser His
1               5                   10                  15

Thr Ser Asp Ile Gly Cys Arg His Arg Lys Asp Pro Pro Arg Ala Pro
                20                  25                  30

Pro Ala Ala Pro Ser Ala Ala Pro Leu Ala Val Thr Trp Leu Ile Arg
            35                  40                  45

Asp Leu Arg Ala Asp Ser Lys Gln Ser Arg Ala Ala
        50                  55                  60

<210> SEQ ID NO 42
<211> LENGTH: 60
<212> TYPE: PRT
<213> ORGANISM: Artificial Sequence
<220> FEATURE:
<223> OTHER INFORMATION: KNP derived peptide #11

<400> SEQUENCE: 42

Gly Leu Leu Ile Ser Cys Phe Gly Arg Arg Ile Asp Arg Ile Ser His
1               5                   10                  15

Thr Ser Gly Ile Gly Cys Arg His Arg Lys Asp Pro Pro Arg Ala Pro
                20                  25                  30

Pro Ala Ala Pro Ser Ala Ala Pro Leu Ala Val Thr Trp Leu Ile Arg
            35                  40                  45

Asp Leu Arg Ala Asp Ser Lys Gln Ser Arg Ala Ala
        50                  55                  60

<210> SEQ ID NO 43
<211> LENGTH: 60
<212> TYPE: PRT
<213> ORGANISM: Artificial Sequence
<220> FEATURE:
<223> OTHER INFORMATION: KNP derived peptide #12

<400> SEQUENCE: 43

Gly Leu Leu Ile Ser Cys Phe Asp Gly Arg Ile Asp Arg Ile Ser His
1               5                   10                  15

Thr Ser Gly Ile Gly Cys Arg His Arg Lys Asp Pro Pro Arg Ala Pro
                20                  25                  30

Pro Ala Ala Pro Ser Ala Ala Pro Leu Ala Val Thr Trp Leu Ile Arg
            35                  40                  45

Asp Leu Arg Ala Asp Ser Lys Gln Ser Arg Ala Ala
        50                  55                  60

<210> SEQ ID NO 44
<211> LENGTH: 60
<212> TYPE: PRT

<213> ORGANISM: Artificial Sequence
<220> FEATURE:
<223> OTHER INFORMATION: KNP derived peptide #13

<400> SEQUENCE: 44

Gly Leu Leu Ile Ser Cys Phe Gly Gly Arg Ile Asp Arg Ile Ser His
1               5                   10                  15

Thr Ser Gly Ile Gly Cys Arg His Arg Lys Asp Pro Pro Arg Ala Pro
            20                  25                  30

Pro Ala Ala Pro Ser Ala Ala Pro Leu Ala Val Thr Trp Leu Ile Arg
        35                  40                  45

Asp Leu Arg Ala Asp Ser Lys Gln Ser Arg Ala Ala
    50                  55                  60

<210> SEQ ID NO 45
<211> LENGTH: 28
<212> TYPE: PRT
<213> ORGANISM: Artificial Sequence
<220> FEATURE:
<223> OTHER INFORMATION: ANP derived peptide #1

<400> SEQUENCE: 45

Ser Leu Arg Arg Ser Ser Cys Phe Asp Gly Arg Met Glu Arg Ile Gly
1               5                   10                  15

Ala Gln Ser Gly Leu Gly Cys Asn Ser Phe Arg Tyr
            20                  25

<210> SEQ ID NO 46
<211> LENGTH: 28
<212> TYPE: PRT
<213> ORGANISM: Artificial Sequence
<220> FEATURE:
<223> OTHER INFORMATION: ANP derived peptide #2

<400> SEQUENCE: 46

Ser Leu Arg Arg Ser Ser Cys Phe Gly Arg Arg Met Asp Arg Ile Gly
1               5                   10                  15

Ala Gln Ser Gly Leu Gly Cys Asn Ser Phe Arg Tyr
            20                  25

<210> SEQ ID NO 47
<211> LENGTH: 28
<212> TYPE: PRT
<213> ORGANISM: Artificial Sequence
<220> FEATURE:
<223> OTHER INFORMATION: ANP derived peptide #3

<400> SEQUENCE: 47

Ser Leu Arg Arg Ser Ser Cys Phe Gly Gly Arg Met Asp Arg Ile Gly
1               5                   10                  15

Ala Gln Ser Asp Leu Gly Cys Asn Ser Phe Arg Tyr
            20                  25

<210> SEQ ID NO 48
<211> LENGTH: 28
<212> TYPE: PRT
<213> ORGANISM: Artificial Sequence
<220> FEATURE:
<223> OTHER INFORMATION: ANP derived peptide #4

<400> SEQUENCE: 48

Ser Leu Arg Arg Ser Ser Cys Phe Asp Arg Arg Met Asp Arg Ile Gly
1               5                   10                  15

Ala Gln Ser Gly Leu Gly Cys Asn Ser Phe Arg Tyr
            20                  25

<210> SEQ ID NO 49
<211> LENGTH: 28
<212> TYPE: PRT
<213> ORGANISM: Artificial Sequence
<220> FEATURE:
<223> OTHER INFORMATION: ANP derived peptide #5

<400> SEQUENCE: 49

Ser Leu Arg Arg Ser Ser Cys Phe Asp Gly Arg Met Asp Arg Ile Gly
1               5                   10                  15

Ala Gln Ser Asp Leu Gly Cys Asn Ser Phe Arg Tyr
            20                  25

<210> SEQ ID NO 50
<211> LENGTH: 28
<212> TYPE: PRT
<213> ORGANISM: Artificial Sequence
<220> FEATURE:
<223> OTHER INFORMATION: ANP derived peptide #6

<400> SEQUENCE: 50

Ser Leu Arg Arg Ser Ser Cys Phe Gly Arg Arg Met Asp Arg Ile Gly
1               5                   10                  15

Ala Gln Ser Asp Leu Gly Cys Asn Ser Phe Arg Tyr
            20                  25

<210> SEQ ID NO 51
<211> LENGTH: 28
<212> TYPE: PRT
<213> ORGANISM: Artificial Sequence
<220> FEATURE:
<223> OTHER INFORMATION: ANP derived peptide #7

<400> SEQUENCE: 51

Ser Leu Arg Arg Ser Ser Cys Phe Asp Arg Arg Met Asp Arg Ile Gly
1               5                   10                  15

Ala Gln Ser Asp Leu Gly Cys Asn Ser Phe Arg Tyr
            20                  25

<210> SEQ ID NO 52
<211> LENGTH: 28
<212> TYPE: PRT
<213> ORGANISM: Homo sapiens

<400> SEQUENCE: 52

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 53
<211> LENGTH: 60
<212> TYPE: PRT
<213> ORGANISM: Bungarus caeruleus

<400> SEQUENCE: 53

Gly Leu Leu Ile Ser Cys Phe Asp Arg Arg Ile Asp Arg Ile Ser His
1               5                   10                  15

Thr Ser Asp Ile Gly Cys Arg His Arg Lys Asp Pro Pro Arg Ala Pro
            20                  25                  30

```
Pro Ala Ala Pro Ser Ala Ala Pro Leu Ala Val Thr Trp Leu Ile Arg
        35                  40                  45

Asp Leu Arg Ala Asp Ser Lys Gln Ser Arg Ala Ala
    50                  55                  60

<210> SEQ ID NO 54
<211> LENGTH: 32
<212> TYPE: PRT
<213> ORGANISM: Homo sapiens

<400> SEQUENCE: 54

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
                20                  25                  30

<210> SEQ ID NO 55
<211> LENGTH: 22
<212> TYPE: PRT
<213> ORGANISM: Homo sapiens

<400> SEQUENCE: 55

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 56
<211> LENGTH: 38
<212> TYPE: PRT
<213> ORGANISM: Dendroaspis angusticeps

<400> SEQUENCE: 56

Glu Val Lys Tyr Asp Pro Cys Phe Gly His Lys Ile Asp Arg Ile Asn
1               5                   10                  15

His Val Ser Asn Leu Gly Cys Pro Ser Leu Arg Asp Pro Arg Pro Asn
                20                  25                  30

Ala Pro Ser Thr Ser Ala
            35

<210> SEQ ID NO 57
<211> LENGTH: 5
<212> TYPE: PRT
<213> ORGANISM: Artificial Sequence
<220> FEATURE:
<223> OTHER INFORMATION: NSFRY

<400> SEQUENCE: 57

Asn Ser Phe Arg Tyr
1               5
```